(12) United States Patent
Goodwin et al.

(10) Patent No.: US 9,914,920 B2
(45) Date of Patent: Mar. 13, 2018

(54) ALTERNATING IONIC MAGNETIC RESONANCE (AIMR) MULTIPLE-CHAMBERED CULTURE APPARATUS

(71) Applicants: Thomas J Goodwin, Kemah, TX (US); Moses J Kushman, Porter Ranch, CA (US)

(72) Inventors: Thomas J Goodwin, Kemah, TX (US); Moses J Kushman, Porter Ranch, CA (US)

( * ) Notice: Subject to any disclaimer, the term of this patent is extended or adjusted under 35 U.S.C. 154(b) by 580 days.

(21) Appl. No.: 13/859,180

(22) Filed: Apr. 9, 2013

(65) Prior Publication Data

US 2013/0267020 A1    Oct. 10, 2013

Related U.S. Application Data

(60) Provisional application No. 61/686,690, filed on Apr. 9, 2012.

(51) Int. Cl.
| | | |
|---|---|---|
| C12M 1/00 | (2006.01) | |
| C12M 3/00 | (2006.01) | |
| C12N 13/00 | (2006.01) | |
| C12M 3/04 | (2006.01) | |
| C12M 1/42 | (2006.01) | |

(52) U.S. Cl.
CPC ............. *C12N 13/00* (2013.01); *C12M 27/10* (2013.01); *C12M 35/02* (2013.01); *C12N 2529/00* (2013.01)

(58) Field of Classification Search
CPC ...... C12M 27/10; C12M 35/02; C12M 35/04; C12N 13/00; C12N 2529/00

USPC ............................................... 435/298.1, 383
See application file for complete search history.

(56) References Cited

U.S. PATENT DOCUMENTS

| | | | | |
|---|---|---|---|---|
| 3,556,000 A | * | 1/1971 | Goodwin | D06C 15/02 100/169 |
| 5,153,131 A | * | 10/1992 | Wolf | C12M 23/24 435/297.2 |
| 6,485,963 B1 | | 11/2002 | Wolf et al. | |
| 2007/0048253 A1 | * | 3/2007 | Goodwin | C12N 13/00 424/85.1 |

(Continued)

FOREIGN PATENT DOCUMENTS

WO    2007038471 A2    4/2007

OTHER PUBLICATIONS miniPERM, miniPERM Lab Scale Protein Production, Jan. 6, 2009, http://greinerbioone.com/UserFiles/File/IVSSbrochure.pdf.*

(Continued)

*Primary Examiner* — Nathan A Bowers
(74) *Attorney, Agent, or Firm* — Benjamin Aaron Adler

(57) ABSTRACT

Provided herein are a culture apparatus, culture systems and an alternating ionic magnetic resonance electromagnetic chamber for culturing cells, tissues or organoid bodies or for delivering a pulsating alternating ionic magnetic resonance field to an object of interest including the above or to an animal, human or plant. The culture apparatus comprises a culture unit having growth and nutrient modules and a randomizing adapter to continually randomize the gravity vector in the growth module. The culture systems further comprise the alternating ionic magnetic resonance electromagnetic chamber.

8 Claims, 10 Drawing Sheets

(56) References Cited

U.S. PATENT DOCUMENTS

2008/0075700 A1     3/2008   Wolf et al.
2010/0178680 A1     7/2010   Goodwin et al.

OTHER PUBLICATIONS

Jackson et al., Small-scale Monoclonal Antibody production In Vitro: Method and Resources, Aug. 1999 http://altweb.jhsph.edu/mabs/ardf/jackson.html.*

* cited by examiner

US 9,914,920 B2

ALTERNATING IONIC MAGNETIC RESONANCE (AIMR) MULTIPLE-CHAMBERED CULTURE APPARATUS

CROSS-REFERENCE TO RELATED APPLICATION

This non-provisional patent application claims benefit of priority under 35 U.S.C. § 119(e) of provisional patent application U.S. Ser. No. 61/686,690, filed Apr. 9, 2012, the entirety of which is hereby incorporated by reference.

BACKGROUND OF THE INVENTION

Field of the Invention

The present invention relates generally to the fields of biophysics, bioelectromechanics, bioengineering, tissue engineering and cellular regeneration. Specifically, the present invention relates to an alternating ionic magnetic resonance (AIMR) multiple-chambered culture apparatus for potentiating or controlling the growth of biological cells and tissues, such as mammalian tissue.

Description of the Related Art

Prior to the development of bioreactors, cell culture was limited to systems subjected to the forces of gravity, with most laboratory cultures producing flat two-dimensional (2D), one cell thick specimens unlike the natural three-dimensional (3D) environment of a complex, multi-cellular organism. Most laboratory experiments therefore had inherent limitations and a strictly one-dimensional view of understanding how cells grew and interacted with one another in their natural environment.

With the development of bioreactors, most of these devices were "stirred tank" bioreactors that used a vertical aspect configuration with a stirring device at the bottom of the growth chamber to mix the cells and fluid medium suspension. Horizontally rotating bioreactors offered a way to minimize or neutralize the sedimentation and shear effects caused by gravity by using the "clinostat principal" in which a fluid medium was rotated about a horizontal axis thus minimizing the wall effects and impeller impacts of internal stirring devices and lowering the overall Reynolds and Coriolis force effect on cells.

Cells grown in rotating bioreactors were suspended in a fluid medium and were continually rotated away from the surfaces of the vessel which enabled cells to adhere to one another and to grow. This type of suspended cell culture resembled growth mechanics in a naturally occurring tissue and in a multidimensional form and thereby promoted more realistic, three-dimensional cell-to-cell contact signaling. These 3D cells were induced to regulate and to produce cellular components as if grown within a complex organism and to produce complex matrices comprising extracellular matrix molecules, proteins, fibers, and other cellular components. These aforementioned processes lead to autoregulation and the ability to self-order in the human mammalian physiology. Inside a complex organism, these components often informed a cell of the neighboring environment and triggered a specific set of responses to that external environment. The cell grew or it became static, which in turn, determined how the cell responded with the production of secondary regulators.

A typical rotating bioreactor had an outer tubular enclosure with transverse end walls and end caps in the end walls. The outer tubular enclosure was supported on input and output shaft members and rotationally driven by an independent drive mechanism. Coaxially disposed within the outer tubular enclosure was a central tubular filter member that was rotationally supported on the input shaft and coupled to the output shaft. The annular space between the inner and outer tubular members defined a cell culture chamber.

Two blade members were positioned about the horizontal axis and extended lengthwise along the cell culture chamber. The blade members had radial arms at one end that were rotationally supported on the output shaft and radial arms at the other end that were coupled to the input shaft. The input shaft was rotationally driven by an independent drive means that normally drove the inner and outer tubular members and the blade members at the same angular rate and direction so that no relative motion occurred between these members. Thus, clinostat motion could be achieved for the particles in the fluid within the cell culture chamber.

Existing bioreactors, however, are overly complicated systems and costly to operate with respect to expenditure of preparation time, upkeep, disposal of non-reusable components. For example, in existing bioreactors the cell samples and any other required initial ingredients must be assembled into the culture system in preparation for an experiment. At the end of the experiment, it is necessary to disassemble significant portions of the culture system in order to extract the cells and/or tissue culture that grew during the experiment. Moreover, because the culture system mechanisms include rotating fluid couplings, leaks may develop over time in the seals of these couplings. Finally, the motors that provide the rotation in existing bioreactors are integral to the system, contributing to the complexity of the system and making it difficult to maintain and operate the system. Accordingly, what is needed is a culture system and method that mitigates or overcomes some or all of the shortcomings of existing bioreactors.

U.S. Pat. Nos. 6,485,963 and 6,673,597 disclose the use of a time-varying electromagnetic force (TVEMF) in a manner that stimulates the proliferation of cells grown in culture. In U.S. Pat. No. 7,179,217, Goodwin et al. disclose the use of a TVEMF sleeve for treatment of an animal limb. Commercial utilization of this technology has provided two approaches to culture system design. The first approach is the use of baffles or plates within the culture system with a time-varying electromagnetic current applied across the plates to induce a time-varying electromagnetic force within the culture chamber. The second approach is to use a coil wrapped around the rotating culture system chamber and affixed thereto with a time-varying electromagnetic current applied to the coil to create a time-varying electromagnetic force within the culture chamber.

There are several limitations with existing culture systems designs that utilize TVEMF in the context of a rotating culture system chamber. First, the existing TVEMF culture systems have the electromagnetic device permanently affixed to the culture chamber unit, which does not allow for the use of disposable modules nor does it accommodate the self-feeding capability of the current invention. Instead, existing systems require periodic and frequent manual exchange of growth media during the culture cycle. Additionally, since the goal of proliferation of cell cultures is in many instances the utilization of the cells and tissues for reintroduction into the human body for tissue regeneration or treatment of human maladies, the culture system chamber must meet the rigid standards of the Food and Drug Administration (FDA). If the EMF inducing device is incorporated into the culture chamber, it significantly complicates the manufacture and sterilization process, and would require routine disposal of the EMF inducing device along with the used culture system chamber. This would significantly add to the cost of the equipment and culturing process for FDA approved purposes.

Another limitation of existing culture systems is that they utilize TVEMF, which does not effectuate the same stimulatory or physiological effect on cultured cells as compared with alternating ionic magnetic resonance. TVEMF fails to stimulate specific ionic species and membrane channel systems that play a major role in the regulation of proliferation, differentiation, tissue repair, and related cellular mechanisms that are inherent to growth, development and maintenance of a mammalian organism. A further limitation is that existing culture systems rely on a batch fed or media perfusion systems to transfer media into and out of the growth chamber. Each of these methodologies fails to provide physiological and homeostatic parameters similar to those of a naturally occurring physiological system.

Thus, there is a recognized need in the art for culture systems that utilize an alternating ionic magnetic resonance field during the three-dimensional culture of cells, including tissues and/or organoid bodies. Particularly, the prior art is deficient in an alternating ionic magnetic resonance system comprising a culturing apparatus that utilizes pre-sterilized and disposable modules and a removable alternating ionic magnetic resonance chamber. The present invention fulfills this long-standing need and desire in the art.

SUMMARY OF THE INVENTION

The present invention is directed to a culture apparatus for growing cells. The culture apparatus comprises means for containing the cells in a growth environment and means for continually randomizing the gravity vector in the growth environment.

The present invention also is directed to a culture system for growing cells. The culture system comprises the culture apparatus described herein, an open-ended chamber having a proximal end with a diameter of a length to receive the growth module therein and an electromagnetic device comprising an electrically conductive material in electrical communication with a conversion device that converts a pulsating time-varying electromagnetic current (PTVEC) into a pulsating Alternating ionic magnetic resonance (AIMR) frequency field. The present invention is further directed to a related culture system further comprising a modulating device configured to produce overlapping or fluctuating alternating ionic magnetic resonance frequencies at one or more modal intervals spanning about 6.5 Hz and ranging from about 7.8 Hz to about 59.9 Hz.

The present invention is directed further to an alternating ionic magnetic resonance (AIMR) electromagnetic device configured to deliver pulsating alternating ionic magnetic resonance to an object of interest. The alternating ionic magnetic resonance electromagnetic device comprises a removable open-ended substantially cylindrical or rectangular chamber comprising an electrically conductive material wound in a square, oval or cylindrical-shaped scaffold thereon and an electrical conversion device that converts a pulsating time-varying electromagnetic current (PTVEC) into a pulsating alternating ionic magnetic resonance (AIMR) frequency field connected electrically to the chamber. The alternating ionic magnetic resonance electromagnetic device also comprises a modulating device that produces overlapping or fluctuating alternating ionic magnetic resonance frequencies at one or more modal intervals spanning about 6.5 Hz and ranging from about 7.8 Hz to 59.9 Hz.

The present invention is directed further still to a culture system for culturing cells, tissue or organoid bodies. The culture system comprises a nutrient module, a growth module, a randomizing adapter, a removable open-ended substantially cylindrical electromagnetic chamber, an electrical conversion device and a modulating device. The nutrient module has a proximal end comprising a first gas-permeable membrane with a gas port disposed thereon and a distal end comprising a first sealable opening. The growth module has a proximal end comprising a second gas-permeable membrane with a plurality of inlet/outlet ports disposed thereon and a distal end comprising a baffling system and a semi-permeable membrane, where the growth module is fluidly connected with the first gas-permeable membrane in the nutrient module. The randomizing adapter has an open proximal end of a diameter sufficient to receive the nutrient module therein, where the distal end of the nutrient module is adaptable to electrically connect with a randomizing mechanism comprising the adapter such that the gravity vector of the growth module fluidly connected to the nutrient module is continually randomized. The removable open-ended substantially cylindrical electromagnetic chamber has a diameter sufficient to receive at least the growth module therein and comprises an electrically conductive wire wound on a square, oval or cylindrical-shaped scaffold thereon. The electrical conversion device converts a pulsating time-varying electromagnetic current into a pulsating alternating ionic magnetic resonance frequency field with a filed strength of about 0.01 Gauss to about 5000 Gauss connected electrically to the electromagnetic chamber. The modulating device produces overlapping or fluctuating alternating ionic magnetic resonance frequencies at one or more modal intervals spanning about 6.5 Hz and ranging from about 7.8 Hz to about 59.9 Hz Other and further aspects, features and advantages of the present invention will be apparent from the following description of the presently preferred embodiments of the invention given for the purpose of disclosure

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 6A depicts calcium ion staining of HBTC cells grown alone exposed (left) and unexposed (right) to alternating ionic magnetic resonance. FIG. 6B depicts calcium ion staining of HBTC cells grown on cultisphere microcarriers exposed (left), unexposed (right) to alternating ionic magnetic resonance and microcarrier control treated with Fura 2AM. FIG. 6C depicts potassium ion staining of HBTC cells grown on cultisphere microcarriers exposed (left) and unexposed (right) to alternating ionic magnetic resonance. FIG. 6D depicts potassium ion staining of HBTC cells exposed to alternating ionic magnetic resonance (top), grown without an electric field (middle) and control microcarriers alone (bottom).

DETAILED DESCRIPTION OF THE INVENTION

Figure 1A:
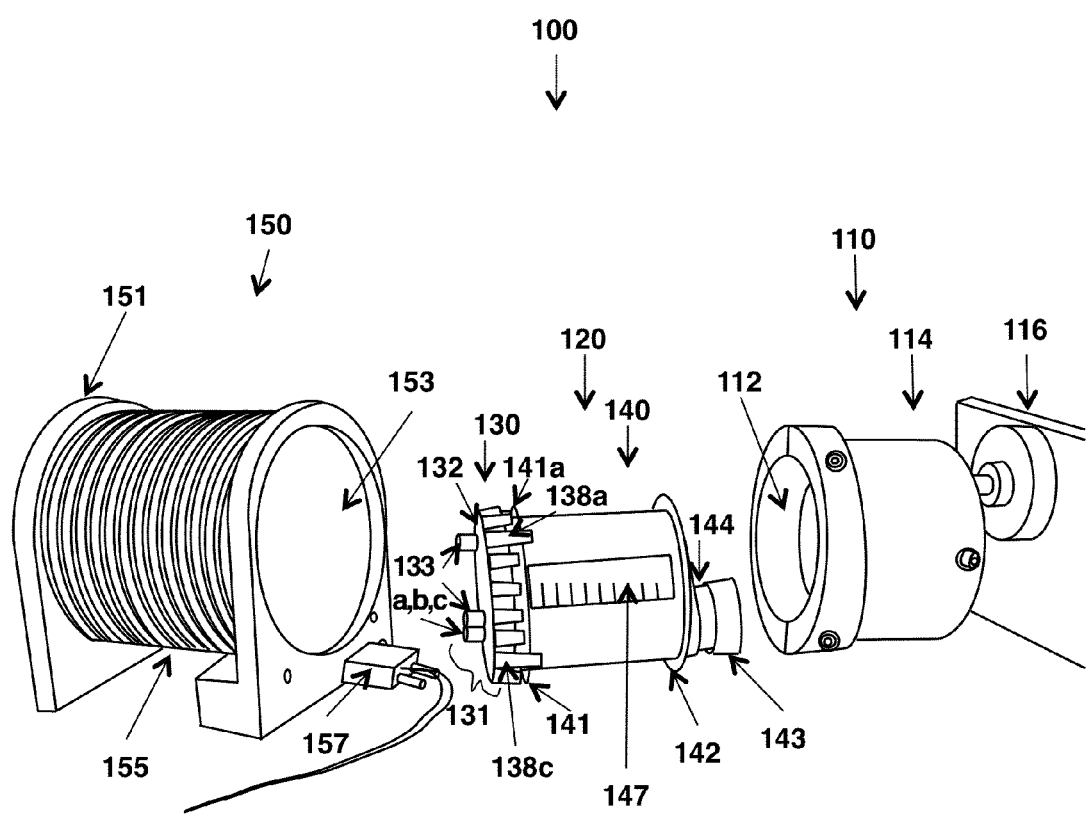
FIGS. 1A-1C is an overview of the unassembled (FIG. 1A), partially assembled (FIG. 1B) and assembled (FIG. 1C) primary components of the culture apparatus comprising a culture unit, a randomizing adaptor and a removable adjustable alternating ionic magnetic resonance module.

As used herein, the term "a" or "an", when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, method steps, and/or methods of the invention. It is contemplated that any device or method described herein can be implemented with respect to any other device or method described herein.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the terms "proximal" and "distal" refer to components or parts thereof or fields that are nearer or farther from the growth module, respectively. With respect to the growth module per se, proximal refers to the side comprising the gas membrane and distal refers to the side comprising the baffling that engages with the nutrient module.

As used herein, the term "animal" refers to a mammal, preferably a human.

In one embodiment of the present invention, there is provided a culture apparatus for growing cells, comprising means for containing the cells in a growth environment; and means for continually randomizing the gravity vector in the growth environment. In this embodiment, the means for containing the cells may be a culture unit comprising a nutrient module and growth module in fluid contact, said cells contained within the growth module. In one aspect, the nutrient module may comprise an open-ended body having a proximal end with a diameter of a length to receive the growth module therein; and a distal end comprising a first sealable opening. In this aspect, the proximal end of the nutrient module comprises a first gas-permeable membrane with a gas port disposed thereon. In another aspect, the growth module may comprise a body having a proximal end comprising a second gas-permeable membrane with a plurality of inlet/outlet ports disposed thereon; and a distal end comprising a baffling system and a semi-permeable membrane in fluid contact with the first gas-permeable membrane.

Further, in this embodiment of the present invention and aspects thereof, the means for continually randomizing the gravity vector in the growth environment may comprise a randomizing adapter having an open proximal end of a diameter sufficient in length to receive the culture unit therein, said distal end of the nutrient module adaptable to electrically connect with a randomizing mechanism comprising the adapter.

In all embodiments, one or both of the nutrient module and the growth module are disposable. Generally, materials comprising the apparatus may be sterilizable. In addition, the cells may comprise virally- or bacterially-infected cells, a tissue, or an organoid body.

In another embodiment of the present invention, there is provided a culture system for growing cells, comprising the culture apparatus as described supra; an open-ended chamber having a proximal end with a diameter of a length to receive the growth module therein; and an electromagnetic device comprising an electrically conductive material in electrical communication with a conversion device that converts a pulsating time-varying electromagnetic current (PTVEC) into a pulsating alternating ionic magnetic resonance frequency field.

Further to this embodiment, the culture system for growing cells comprises a modulating device configured to produce overlapping or fluctuating alternating ionic magnetic resonance frequencies at one or more modal intervals spanning about 6.5 Hz and ranging from about 7.8 Hz to about 59.9 Hz. In this further embodiment, the overlapping or fluctuating alternating ionic magnetic resonance frequencies produced are about 10, 14, 15, 16, or 32 Hz. Further still one or more of the alternating ionic magnetic resonance frequencies produced may fluctuate between about 8 and 14 Hz.

In both embodiments, a representative electrically conductive material includes but is not limited to a copper wire or ferromagnetic wire wrapped about a non-conductive or conductive core at about 5 to about 500 turns per inch. Representative electrical conversion device include but are not limited to a random waveform generator, an amplifier, an antenna, or other transmission device. Also, the alternating ionic magnetic resonance field may have a field strength of about 0.01 Gauss to about 5000 Gauss.

In yet another embodiment of the present invention, there is provided an alternating ionic magnetic resonance electromagnetic device configured to deliver pulsating alternating ionic magnetic resonance to an object of interest, comprising a removable open-ended substantially cylindrical or rectangular chamber comprising an electrically conductive material wound in a square, oval or cylindrical-shaped scaffold thereon; an electrical conversion device that converts a pulsating time-varying electromagnetic current into a pulsating alternating ionic magnetic resonance frequency field connected electrically to the chamber; and a modulating device that produces overlapping or fluctuating alternating ionic magnetic resonance frequencies at one or more modal intervals spanning about 6.5 Hz and ranging from about 7.8 Hz to 59.9 Hz.

In this embodiment the alternating ionic magnetic resonance frequencies may range from about 8 Hz to about 14 Hz. Also in this embodiment the electrically conductive material may be copper wire or ferromagnetic wire wrapped around a non-conductive or conductive core at about 5 to about 500 turns per inch. In addition, representative objects of interest include but are not limited to an animal, human, plant, appendage, limb, organ, tissue, culture or cell growth apparatus. Furthermore, the alternating ionic magnetic resonance field may have a field strength of about 0.01 Gauss to about 10,000 Gauss.

In yet another embodiment of the present invention, there is provided a culture system for culturing cells, tissue or organoid bodies, comprising a nutrient module having a proximal end comprising a first gas-permeable membrane with a gas port disposed thereon and a distal end comprising a first sealable opening; a growth module having a proximal end comprising a second gas-permeable membrane with a plurality of inlet/outlet ports disposed thereon and a distal end comprising a baffling system and a semi-permeable membrane, the growth module fluidly connected with the first gas-permeable membrane in the nutrient module; a randomizing adapter having an open proximal end of a diameter sufficient to receive the nutrient module therein, the distal end of the nutrient module adaptable to electrically connect with a randomizing mechanism comprising the adapter such that the gravity vector of the growth module fluidly connected to the nutrient module is continually randomized; a removable open-ended substantially cylindrical electromagnetic chamber with a diameter sufficient to receive at least the growth module therein and comprising an electrically conductive wire wound on a square, oval or cylindrical-shaped scaffold thereon; an electrical conversion device that converts a pulsating time-varying electromagnetic current into a pulsating alternating ionic magnetic resonance frequency field connected electrically to the electromagnetic chamber; and a modulating device that produces overlapping or fluctuating alternating ionic magnetic resonance frequencies at one or more modal intervals spanning about 6.5 Hz and ranging from about 7.8 Hz to about 59.9 Hz.

The present invention provides an apparatus, systems, models, and methods for the short and long-term proliferation, growth, enrichment, conditioning, modification, and/or aggregation of mammalian cells, tissues or organoid structures in adaptable culture systems in alternating ionic magnetic resonance fields. Alternating ionic magnetic resonance fields comprise specific bio-electromagnetically relevant frequencies that mimic the global diurnal cycle believed to influence cellular behavior and genetic evolution. Particularly, an alternating ionic magnetic resonance field, such as produced in the alternating ionic magnetic resonance chamber presented herein, mimics in part the natural environment that mammalian cells are exposed to in an earth-based living system.

Generally, the culture system comprises a gravity randomizing, multiphasic culture system having a disposable self-feeding growth module, a nutrient and growth module that comprises a culture unit which, optionally, is disposable, and a removable electromagnetic chamber or unit which, when applied to the outside of a culture unit, is suitable for delivering alternating ionic magnetic resonance fields to the contents of the culture unit. Existing culture systems using PEMF and TVEMF have been shown to increase the rate of cell growth of the cells cultured in the system. The alternating ionic magnetic resonance culture system is a significant improvement on these systems and incorporates instead the use of an alternating ionic magnetic resonance device which induces cell regeneration, increases cell fidelity, modulates cellular transcription and induces the selective regulation of key physiological genes useful in directing the differentiation and dedifferentiation process of particular cells.

The generated alternating ionic magnetic resonance field, as described herein, produces a series of controlled resonating waveforms that mimic the Schumann Resonances, which are global electromagnetic frequencies that are excited by lightning discharges, with more precision than are created naturally. The alternating ionic magnetic resonance-generated resonating waveforms can be modified or accelerated to specifically regulate or induce a physiological response in a particular cell system, i.e., a pulsed emission to preferentially effect the oscillation of specific ion species in the living cell. Each cell type has the potential to respond to a given resonating pattern differently than another cell type based on total ion content and ion species. Moreover, each physiological response may involve the induction of different cellular control mechanisms, such as, but not limited to, stimulated or decreased genomic, proteomic, transcriptomics, and metabolomic expressions, altered ion flow through the membrane, and altered gene replication.

Thus, the alternating ionic magnetic resonance culture system and apparatus and methods for use can stimulate the expression and regulation of various genes, including transcription factors, and to alter the activity of the genome to result in modified output of existing cellular proteins, such as cell transport proteins involved in regulating ionic concentration, membrane transport and other crucial pathways in the regulation of growth, development, and differentiation, dedifferentiation, cell maintenance, inflammation, and aging-related mechanisms in animals and plants. Use of the alternating ionic magnetic resonance culture system, apparatus and the methods to stimulate gene expression and regulation, is relevant to both practical commercial applications as well as applications relating to investigations that focus upon re-creating initial conditions in the context of evolutionary biological processes at the cellular and physiological level.

The alternating ionic magnetic resonance culture system and apparatus also offers the ease and convenience of using disposable components for ready compliance with rigid FDA requirements addressing cleanliness and the avoidance of cross-contamination of cell species. The use of a disposable culture unit facilitates the manufacture and use of a system that can easily meet the strict requirements of the FDA. Components can be manufactured and packaged in sterile packs for ready use by one of ordinary skill in the art, much the same as other disposable medical devices are used. The alternating ionic magnetic resonance chamber of the current invention facilitates selective reuse of the ionic magnetic resonance (IMR) device, which contributes to minimizing the costs associated with culturing cells and tissues for medical purposes.

The alternating ionic magnetic resonance culture system comprises a culture unit, which has a pre-sterilized, disposable, self-feeding growth module and a pre-sterilized disposable nutrient module, a removable and interchangeable alternating ionic magnetic resonance electromagnetic chamber, and a means for continually randomizing the gravity vector of the growth module and nutrient module, such as a randomizing adapter. The pre-sterilized and disposable components minimize cumbersome handling, costs and difficulties associated with the improper delivery of the IMR fields in known culture systems and EMF and TVEMF designs.

Alternatively, the growth and nutrient modules may comprise reusable materials and the alternating ionic magnetic resonance chamber may be disposable.

The randomizing adapter holds the culture system in a horizontal position, whereby a basically cylindrical culture system can rotate or move clockwise and/or counter clockwise horizontally about its central radial axis to minimize adherence of the cells to the reactor walls. The randomizing adapter comprises a randomizing device or mechanism for continually randomizing the gravity vector in the growth module or culture system alone within a stationary nutrient module and a stationary electromagnetic device, in unison with an electromagnetic device located inside a stationary nutrient module or together with the nutrient module and electromagnetic device.

A continuously randomized culture system provides a three-dimensional growth environment effectuated by continual gravity randomization, steady but consistent disruption, such as oscillation. Minimal turbulence randomization discourages adherence of eukaryotic cells to the walls of the culture system while encouraging self-adherence of the cells to one another. The randomizing adapter accommodates rotations or oscillations of at least the growth module sufficient to minimize adherence of the cells to the walls of the chamber. Different cell types have different adherence factors, so depending on the type of cells to be cultured, the optimal rate of rotation will fluctuate. The adherence factor will also become more important as the cells proliferate within the chamber and become more concentrated, whereby there is more interaction with the wall of the chamber. As such, the rate of rotation or oscillation of the chamber often increases as the density of cells increases in longer runs in the culture system. Consequently, the continually randomized gravity vector device optimally comprises a variable setting that can accommodate growth chamber rotation speeds in the range of 0.01 to 60 rpm, with a preferred range of 2 to 40 rpm. In systems using an oscillating type of device, periodic oscillations may range in frequency from being continuous to oscillating every 30 seconds or even every half hour.

The randomizing adapter may be a simple system of external rollers on which the culture system sits, similar to typical tissue culture roller bottle mechanisms. Alternatively, rotation can be effectuated by an external electric motor using a system of fan-belt like connection mechanisms or a direct drive. The randomizing mechanism may systematically rotate the entire culture system or the culture unit or the growth module alone. The type of rotation device will dictate the type of adapter necessary on the component parts, such as a pulley-like wheel that would be firmly attached to a spindle incorporated into to the affixed growth module cap and extends through a sterile liquid tight adapter in the nutrient module cap.

The growth module contains a small volume of culture media, as well as the cells and/or tissue and, optionally, a matrix material to be cultured, that completely fills the module with no noticeable air space. It has an integral semi-permeable molecular membrane incorporated into one of its walls to facilitate the diffusion of gases, nutrients and wastes between the cell culture chamber and the extra nutrient-rich media in the surrounding nutrient module. The molecular membrane of the growth module contains a diffusible osmotic membrane capable of exclusion thresholds from 100-500,000 MW with a preferable cutoff range of 2000-12500 MW. The osmotic semi-permeable membrane is generally composed of a hydrophilic composition, but may comprise a more structural composite coated with a hydrophilic composition (e.g., nitrocellulose, polysulphone, polyacetate, or other similar composite). Unlike a perfused system, the semi-permeable membrane system facilitates the transport of nutrients and wastes without the loss of valuable biomolecules from the growth module. The retention of these biomolecules increases the accuracy and fidelity of the mammalian organoid recapitulation. Additionally, the specific membrane exclusion cut off provides a means to enhance the production of valuable cellular proteomics. This enhancement saves time, effort and purification costs. The growth module also comprises a means for securement.

The nutrient module may be disposable and serves as a media reservoir that attaches to or surrounds the growth module. The nutrient module has at least one sealable opening at one end, which is sealable with an appropriate cap, e.g., screw-top, snap-top, crown-top, crimped-top, slide-top, and designed to be large enough to insert an appropriately sized growth module therein. The cap may have an adapter assembly for connecting an external movement device capable of delivering a continual randomized movement to the growth module or culture system, for example, oscillating or rotating in a mono- or bidirectional manner. Preferably, the entire culture system is attached via the wall of the nutrient module to a bidirectional motor device that slowly randomizes the gravity vector of the entire system.

The nutrient module supplies a continually diffusible supply of fresh material to the cultured cells and is adapted with a gas port or gas exchange vent fitted with a semi- or gas-permeable membrane to provide for the exchange of waste gases. Carbon dioxide and ammonia generated by the tissues in the growth module diffuse out of nutrient module and atmospheric, i.e., 159 mm Hg, oxygen diffuses into the nutrient module through the gas-permeable membrane of the gas port. The gas permeable membrane may be a dialysis membrane, a thin gas-permeable silicone membrane or a similar material. The gas port may be incorporated into the nutrient module cap for convenience or may be located in the wall of the nutrient module as a separate opening to the outside environment. The nutrient module includes a mixing device located externally to the gas permeable membrane.

These processes maintain homeostatic physiological conditions in the culture much as seen in the human or mammalian body. The nutrient module is large enough to accommodate the full volume of the growth module in addition to a sufficient volume of media to effectuate efficient exchange of nutrients and oxygen from the fresh media to the growth module and waste products and gases away from the growth module for removal from the system.

The growth module may be disposable and/or an internal module and is typically a cylindrical container, although it may be any shape, such as, but not limited to, a sphere or bag. The growth module has a sealable opening at one end that is fitted with and sealed with an appropriate sterile, liquid-tight cap, for example, screw-top, snap-top, crown-top, crimped-top, slide-top, that may have one or more ports for easy assembly, injection, inoculation and harvest. The sterile liquid-tight cap provides also for the growth module cap to fit into a liquid-tight randomizing adapter that allows for rotation of the growth module. The growth module may be adapted with inlet and outlet ports for the periodic or continual exchange of media through the chamber and may be equipped with a baffling system that efficiently directs a slow continual flow of fresh media and nutrients across the osmotic membrane to allow more control over nutrient transport between the modules to aid in maintaining a more controlled, homeostatic environment. Such a baffling system streamlines the use of fresh media and has the potential of decreasing the overall amount of media needed during the course of a culture experiment.

One wall of the growth module at least partially comprises a semi-permeable, hydrophilic dialysis membrane that contains the cells and/or tissue within the confines of the growth module while allowing the free diffusion of gases, nutrients and metabolic wastes with the fresh media in the nutrient media-hold compartment. A second wall in the growth module comprises a gas permeable membrane that is hydrophobic and controls the resident dissolved gas coefficient in the growth module.

The dialysis membrane may be any material with pores large enough for the transfer of small molecules, but small enough to retain intact cells within the growth module. It may comprise a gas-permeable silicone composition or a polyethylene type material that provides for efficient transport of carbon dioxide, dissolved in the culture medium, both as a gas and as a solute in the form of sodium bicarbonate from the growth module to the nutrient module and for the transport of oxygen into the bioreactor. The dialysis membrane may be covered with an additional support or membrane stabilizer that protects the dialysis membrane from mechanical damage during handling, setup and harvest, as well as during the culture stage to prevent damage from moving or swirling media in the modules.

In addition to permitting transport of carbon dioxide and oxygen, the dialysis membrane is selected to have a pore size sufficient to permit the diffusion of other solubilized nutrients, such as sugars, amino acids, vitamins, ions, etc., from the fresh media in the nutrient module to the growth module, as well as the transfer of metabolic byproducts, such as acidic compounds, for example, lactic acid, toxic gases, e.g. carbon dioxide, toxic solutes, e.g. ammonium ions, and other low molecular mass products from the growth module to the nutrient module. The pore size must be small enough, however, to prevent the transfer of cells and high molecular weight cell products, such as, secreted proteins, antibodies, glycoproteins, large nucleic acids, etc., into the nutrient module.

The growth module may be disposed inside a larger nutrient module. The growth module may be filled with cells/tissue and media, and sealed prior to insertion into the nutrient module, or may be inserted empty and assembled inside the nutrient module, and later filled and sealed while inside the nutrient module. The ability to remove the growth module and move it to another nutrient module facilitates subsequent processing of the cultured cells/tissues with minimum hazard of contamination and loss of time and efficiency.

In one non-limiting example of a culture unit, a 35 ml or 50 ml capacity growth module is fitted to a 450 ml nutrient module by a snapping or other connection mechanism or means. The outer nutrient module holds sufficient media to provide support of cell growth inside the smaller growth module for a period of several days or more. In another non-limiting example of a culture unit, the nutrient module is significantly and substantially larger than the growth module whereby the volume of the media-hold compartment now exceeds the volume of the growth module by as much as 100,000 fold. For instance, one or multiple small 1-5 cc growth module(s) may be completely submersed in a 100-liter nutrient module (similar to a 25-30 gallon bacterial fermentation tank), or one or more rod(s) comprising multiple tandem units of smaller 1-5 cc growth modules may be submersed in an elongated cylindrical nutrient module. This is more conducive for periodic manual exchanges of media.

Preferably, a larger nutrient module having a volume 2 to 50 times that of the growth module is used. With larger nutrient modules, manual exchange of the media at periodic time intervals without having to continually feed fresh media into the module is possible. As such, culture units having larger nutrient modules need not have inlet and outlet ports for media exchange, but, optionally, may have one or more sets of ports for convenience in handling the media. Culture units requiring periodic manual exchange of the media would preferably have nutrient module volumes greater than 10 times that of the growth module.

The growth and nutrient modules may be made of disposable biocompatible polycarbonate based materials that can be autoclaved under controlled conditions for reuse if necessary, or they may be made of more durable components such as glass or stainless steel or polycarbonates/plastics. The growth module comprising the dialysis membrane is more adapted to irradiation type sterilization and better for prepackaged blister-like manufacture and sterilizing. The nutrient module can be reused and may be made of polycarbonate or a more stable material such as glass or stainless steel.

The alternating ionic magnetic resonance chamber comprises an electromagnetic modulating device configured to deliver a pulsating alternating ionic magnetic resonance field to cultured cells/tissue, organoid bodies, etc. within the growth module. The electromagnetic device may comprise an electrode or set of electrodes or a removable chamber that is easily interchangeable depending upon the needs of the system. Preferably, the alternating ionic magnetic resonance chamber is an easily removable chamber that encompasses or fits around or receives therein the entire culture system or only the growth chamber. In the form of a removable chamber, the chamber is a slip-on chamber that holds a coil designed to be larger than the diameter of the culture unit. It is made of a relatively rigid electrical conductive material, e.g., a wire, wound in a cylindrical or rectangular shape that when connected to a pulsating electromagnetic current creates a electromagnetic force in the range of about 0.001 to about 10,000 Gauss within the internal portion of the chamber and the encompassed culture device.

Preferably, the conductive wire of the alternating ionic magnetic resonance chamber is made of a conductive ferromagnetic material coiled about an electromagnetic permeable polymer at about ten coils per inch. The coil can be encased in a thin flexible encasement made of a smooth conductive material that provides for easy handling during assembly and disassembly of the culture system and convenient cleaning before and after use. Also, the alternating ionic magnetic resonance field may be generated by a device producing a pulsating time-varying current passed through a conductor with an RMS value of about 0.01 to about 10000 mA, with a preferred range of about 1 to about 5,000 mA for some cell systems.

The alternating ionic magnetic resonance protocol/signal can be generated by many commercially available devices that are commonly referred to as random/arbitrary waveform or waveform generators, such as units produced by Tektronics, e.g., models AFG3021B, AFG3022B, AFG3101, AFG3102, AFG3251, AFG3252; and Agilent, e.g., models 33220A, and 33250A 33220A-HO1, among numerous other suppliers. The waveform generator is programmed to produce the desired series of pulses at the desired frequencies over a specific time interval. This signal is then connected to the output or transmission device either directly or though an amplifier to strengthen/regulate or increase the intensity of the field if desired. Alternatively, the "signal or waveform protocol" is programmed onto a custom designed computer chip and the series of desired signals are emitted from the chip to the transmission device after it is energized via a power supply that will produce the desired field strength in the transmission device.

The alternating ionic magnetic resonance field is a multivariant field and may be induced by either a multi varying current within a conductor or by a multi varying voltage between fixed conductors. For example, the culture is placed near a conductor through which a time-varying current is passed. Alternatively, the culture is placed between parallel plates upon which a time-varying voltage is applied. In both cases, an alternating ionic magnetic resonance results within the region of the cell culture.

Several methods can be used to produce an alternating ionic magnetic resonance signal, such as delta or square wave, Fourier curve or a combination of signals within a given time domain. For example, an array of conductive current carrying (voltaic) electrodes can be arranged to focus the electromagnetic (EM) field in the specific chamber holding a culture. An alternating ionic magnetic resonance can also be applied to enhance tissue growth that may occur on a shaped or custom designed substrate within the chamber. The electromagnetic field may be generated by various means, such as, by directing the current waveform directly through a conductive substrate or substrate layer or by projecting the field from an external electrode, for example, a plate, an antenna, a coil, or a chamber, or from a set of electrodes adjacent to and spaced apart from, but in the immediate vicinity of, the medium, so that the relative strength of the electromagnetic field is effective within the growth chamber. For example, a current of about 100 milliamps, conducted between opposite corners of a metallic conductor, produces a stimulatory alternating ionic magnetic resonance extending several centimeters from the plate surface.

Particularly, when the alternating ionic magnetic resonance field is generated through conductive antennae, external or in direct contact with the media, e.g., wire, electrode, coil or similar transmission device, the field is adjacently spaced apart from the cultured cells and media and carries an alternating ionic magnetic resonance signal advantageously produced by a varying electrical potential in the form of a delta or square wave having the preferred fundamental frequencies of approximately 10-300 cycles per second (Hz). Particularly, one or more overlapping or fluctuating alternating ionic magnetic resonance frequencies at fundamental intervals of 10, 14, 15, 16, or 32 Hz, and, optionally, resonances that fluctuate between about 8 and 14 Hz (rounded values) can be produced and passed through the antennae or transmission device. The fundamental intervals include the respective harmonic intervals extending to 256 Hz, and incorporating all harmonics of the aforementioned fundamental frequencies to infinity in the form of a square wave of 0.01-10000 mA with a nearly zero time average Preferably, a two-dimensional or a three-dimensional directional antennae may be utilized and may be applied to conventional two-dimensional or to three-dimensional tissue cultures. Three-dimensional cultures may be achieved in actual microgravity or by continually randomized gravity vector vessel technology that simulates some of the physical conditions of microgravity, and/or in other, conventional three-dimensional matrix based cultures. The electromagnetic field, preferably an alternating ionic magnetic resonance field, is achieved in the vicinity of the antennae or coil by passing, through the directional device, a pulsating electromagnetic field of the correct frequency, duration, and field strength, for the proper duration.

During use of the culture system the range of frequency and oscillating electromagnetic field strength is a parameter that may be selected to achieve the desired stimulation of the cultured material, such as tissues, cells or genes, etc. of interest. The final field produced can be in the range of 0.001 to 10000 Gauss, but the preferred range inside the central region of the chamber cylinder and the growth module of the culture system is in the range of about 0.01 to about 5,000 Gauss.

Thus, the present invention provides methods for three-dimensional growth of a culture material, such as, but not limited to, animal, preferably mammalian, cells, tissues, organoid bodies, etc. The culture material is introduced into the growth module and grown in the nutrient-rich media provided by the nutrient module in the presence of an alternating ionic magnetic resonance field. During growth the gravity vector of the culture unit is randomized to favor three-dimensional growth. This maximizes the efficiency of metabolic exchange within the system while simultaneously providing for the accumulation of valuable biomolecules in the growth module and the nutrient module. A more controlled cell growth culture system is thus enabled that can be manipulated to provide for increased rate of cell growth, faster differentiation, increased cell fidelity, and the induction or suppression of selective physiological genes involved in directing cellular differentiation.

Specific culture material may be selected and conditions set to regulate, for example, gene expression and protein activity within the cultured material. The alternating ionic magnetic resonance field stimulates the expression and regulation of various genes, including transcription factors, and alters the activity of the genome. This results in a modified output of existing cellular proteins, such as cell transport proteins involved in regulating ionic concentration, membrane transport and other crucial pathways in the regulation of growth, development, and differentiation, dedifferentiation, cell maintenance and aging-related mechanisms in animals and plants. Regulating cell differentiation/dedifferentiation via the methods and processes provided herein may facilitate the development of faster healing and lifespan extension compositions and applications.

In systems where it is desired to have the cells adhere to substrates for the sole purpose of proliferation without promoting three-dimensional tissue growth, the cells can be grown directly on a flat, two-dimensional electrode surface composed of a biocompatible material. In these situations, some cultured cells may actually be attracted to the supportive electrode material, coatings, or electrically conductive channels that can be incorporated into the culture unit to facilitate cell attachment. For example, the alternating ionic magnetic resonance field is induced in the region of the channel by passing the alternating ionic magnetic resonance protocol through a conductor placed along the channel.

In some systems microcarrier spheres or beads are included and suspended within the culture medium to induce adherence of the cells to the beads. For cell proliferation in these systems, the culture system growth module is preferably exposed to the randomization at a range of about 2 to 60 rpm, and the alternating ionic magnetic resonance is generated by a time-varying current passed through a conductor with an RMS value of about 0.001 to 10,000 Gauss with a preferred range of about 0.01 to 3000 Gauss.

Particularly, the present invention provides methods for up-regulating or increasing viral replication and proliferation genes and gene products in a culture material, such as, cells, tissue, etc. Culture material infected with a virus of interest, grown in the alternating ionic magnetic resonance culture system induces the up-regulation of genes associated with the virus, particularly, those associated with replication and proliferation. In non-limiting examples, such models and systems would be useful for producing large numbers of virions for vaccine production, identification of viral genomic adaptation products, tracking of viral genomic shift during a long term culture, development of antivirals or antibacterials targeted at blocking replication, and harvest of human cell-produced proteins that only result from virally or bacterially infected cells. Correspondingly, the methods provided herein are applicable to culture materials infected with or grown with a bacteria of interest to up-regulate bacterial-associated genes. Methods of identifying proteins or other products from the media comprising the culture system are well-known in the art as are methods for development of antivirals and an antibacterials based on specific compounds, proteins, nucleic acids, etc.

Moreover, the present invention provides models of 3-dimensional tissue-like assemblies (TLAs) of cells. The tissue-like assemblies are stable for at least 3 months, preferably 6 months or longer and share features with the corresponding 2-dimensional tissues/cells or with tissue/cells obtained in vivo. The cells may be grown with or without an alternating ionic magnetic resonance field. Alternatively, the model may comprise tissue-like assemblies of cells infected with a virus or a bacteria, particularly a pathogen. These tissue-like assemblies also remain stable for at least three months. Moreover the viral or bacterial genome remains stable throughout the infection period. Such models are useful for, but not limited to, the up-regulation of viral or bacterial associated or induced genes and/or gene products and/or the study of viral or bacterial adaptive mechanisms.

A preferred embodiment of the alternating ionic magnetic resonance culture system is depicted in the figures and described below. However, such reference is not meant to limit the present invention in any fashion. The embodiments and variations described in detail herein are to be interpreted by the appended claims and equivalents thereof.

As shown in an unassembled view in FIG. 1A, the alternating ionic magnetic resonance culture apparatus 100 comprises a randomizing adapter 110, a culture unit 120, and an AIMR chamber 150. The randomizing adapter has an open, circular proximal end 112 with a diameter sufficient to accommodate the culture unit therein and a distal end 114 in electrical communication with a randomizing mechanism 116. The culture unit comprises a growth module 130 at the proximal end and a nutrient module 140 at the distal end of the culture unit into which the growth module is fitted and secured at least via a securing or fastening means 138a,b to a lip, rim or edge 141a comprising the proximal end 141 of the nutrient module. The growth and nutrient modules are shown here comprising substantially cylindrical bodies, however the modules may have other shapes as long as the nutrient module can securely and functionally accommodate the growth module and contain nutrient media therein and the growth module can securely and functionally contain a culture material for growth therein and receive and exchange nutrient media and gases.

Figure 2A:
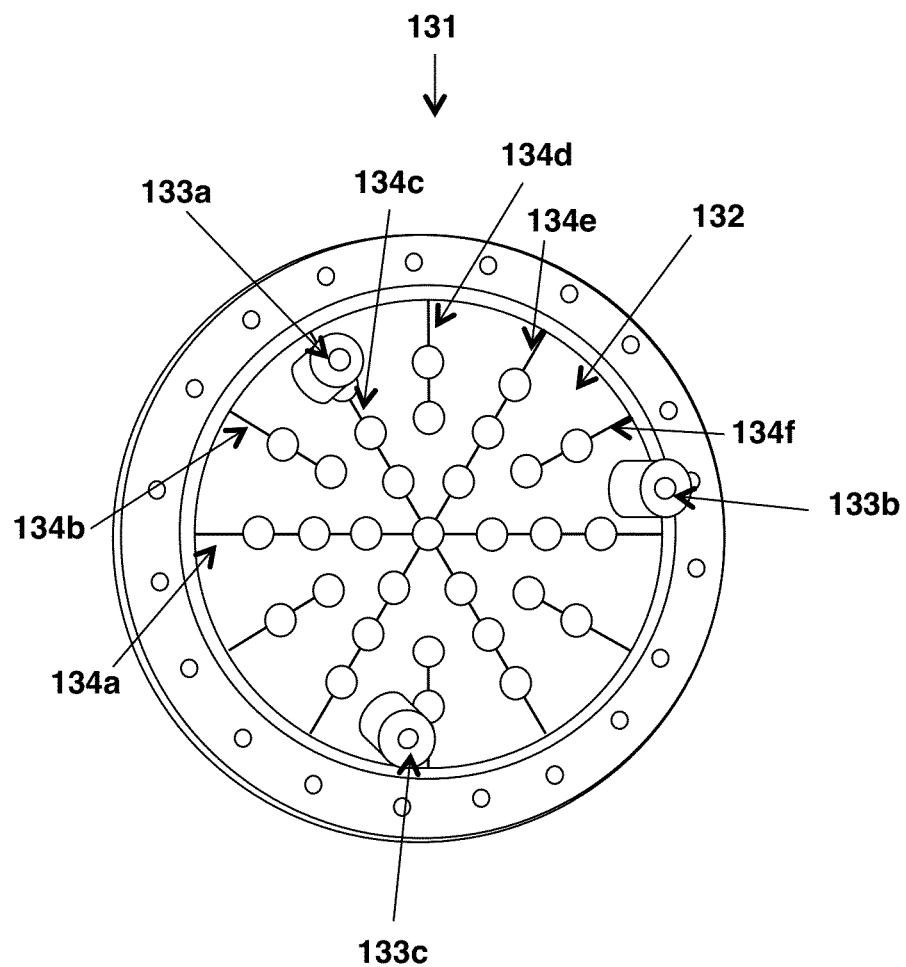
FIGS. 2A-2B are front (FIG. 2A) and back (FIG. 2B) views of the growth module.

The growth module 130 has a front or proximal wall 131 comprising a gas membrane 132 and inlet and outlet ports 133a,b,c disposed through the gas membrane (see FIG. 2A). The back or distal wall of the growth module comprises a baffling means or system 136 which when affixed to the proximal end 141 of nutrient module is in fluid communication therewith (see FIG. 2B). The proximal end 141 of the nutrient module comprises a gas port or gas exchange vent 145 fitted with a semi- or gas-permeable membrane 146 (see FIG. 3). The distal end 142 of the nutrient module comprises a cap 143 covering an opening 144 into the nutrient module that is adaptable to engage with the randomizing mechanism. Optionally, the nutrient module may comprise a means for indicating media volume 147 etched or disposed on the module surface. The AIMR chamber 150 has circular proximal 151 and distal 153 ends with a diameter sufficient to slide or fit over the culture unit and comprises an electromagnetic device 155, in this instance a coil, disposed around the exterior thereof and means or device 157 for generating a pulsating, time-varying electromagnetic current (PTVEC) in electrical communication with the electromagnetic device.

Figure 1B:
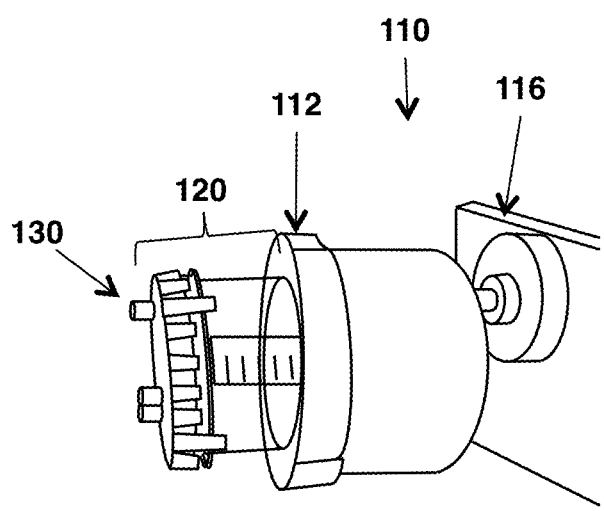
Figure 1C:
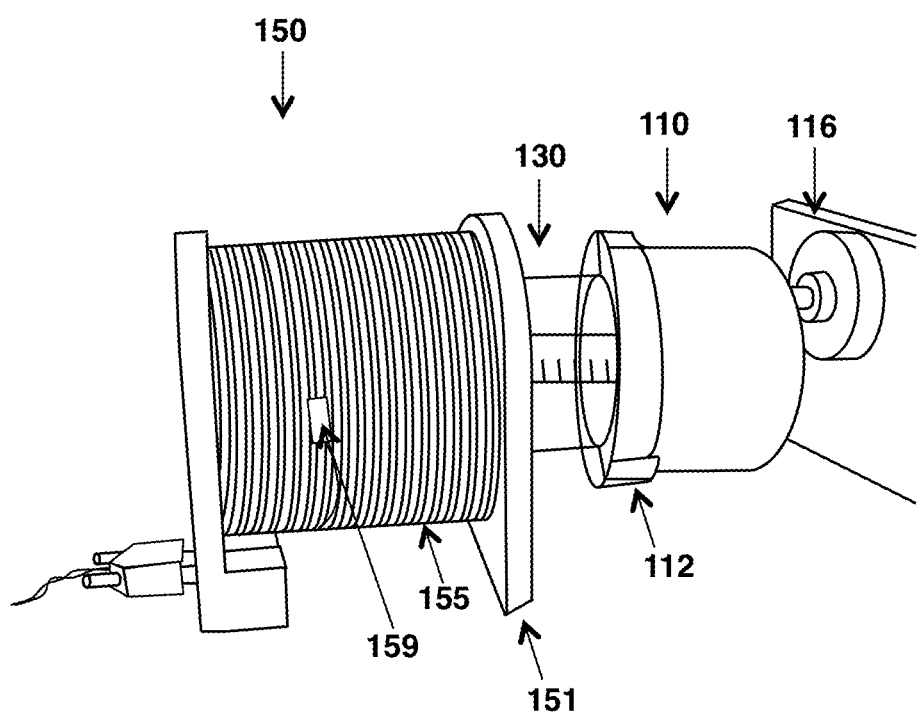

FIG. 1B illustrates how the culture unit is accommodated within the randomizing adapter. The distal end 142 of the nutrient module 140 comprising the culture unit 120 is disposed within the proximal end 112 of the randomizing unit 110 and is electrically engaged with the randomizing mechanism 116 (not shown). This leaves the growth unit 130 uncovered and available to receive an alternating ionic magnetic resonance field. Assembled, as shown in FIG. 1C, the proximal end 151 of the AIMR chamber 150 is disposed around the proximal end 141 of the nutrient module, particularly such that at least the growth module 130 is disposed within the alternating ionic magnetic resonance chamber to receive the alternating ionic magnetic resonance field generated by the electromagnetic device 155. A pulse sensor 159 is disposed on the electromagnetic device.

With continued reference to FIGS. 1A-1C, FIG. 2A is a front view of the growth module 130. The front or proximal side 131 of the growth module comprises a gas membrane 132 disposed across the surface thereof. The gas membrane comprises a plurality of protrusions, generally represented by 134a,b,c,d,e,f, radially disposed across the surface of the membrane to increase the surface area and has a plurality of inlet/outlet ports represented as 133a,b,c disposed through the membrane and in fluid communication with nutrient media contained within the growth module.

Figure 2B:
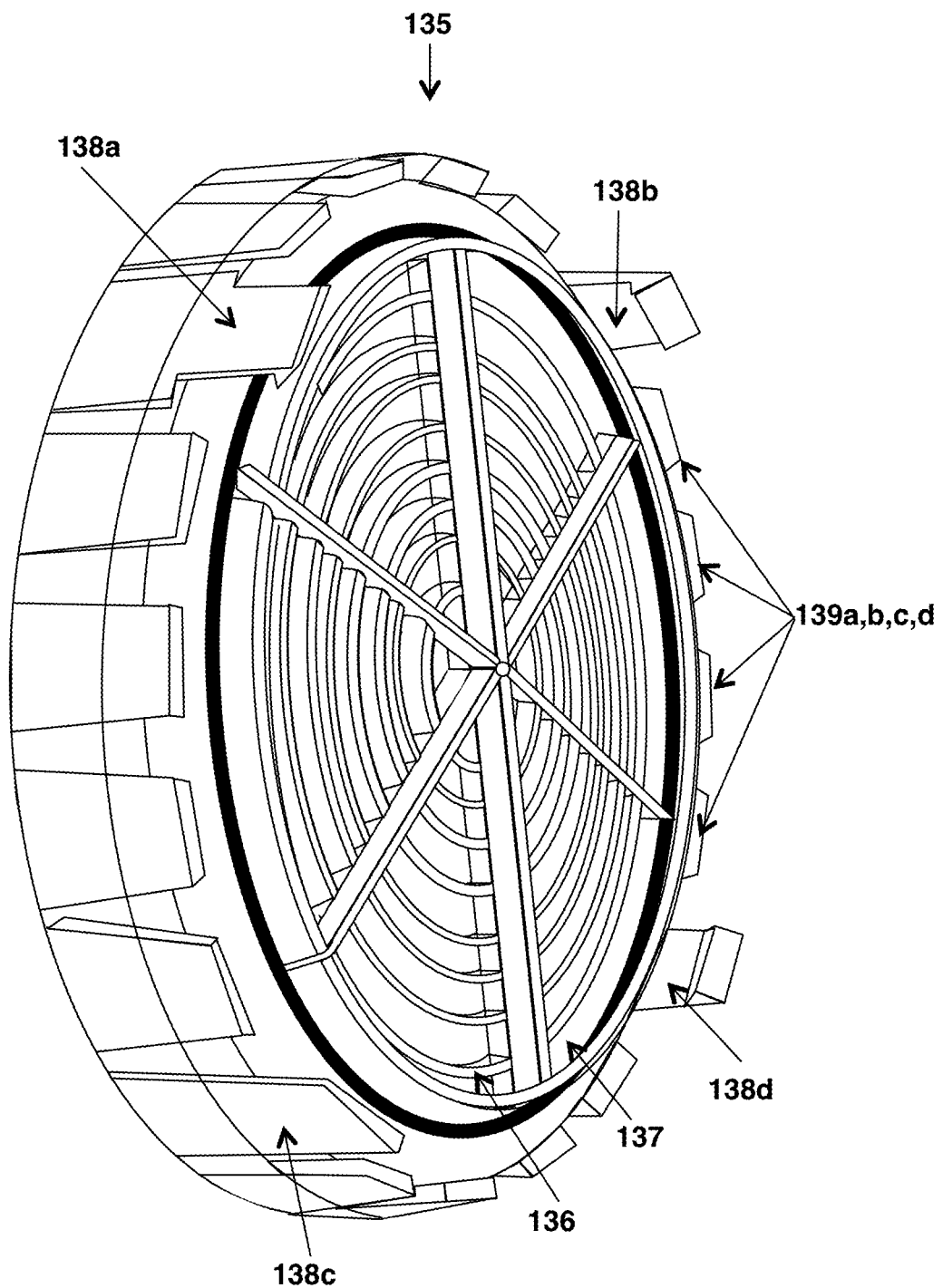

FIG. 2B is a back view of the growth module 130. The back or distal side 135 comprises a baffling system 136 disposed therein and a semi-permeable dialysis membrane 137 comprising at least part of the distal side. The gas-permeable membranes 132 and 146, including the inlet/outlet ports 133a,b,c and the gas port 145 are in fluid contact with the nutrient media in both the growth module and the nutrient module. The outer edge of the growth module comprises a plurality of a first securing or fastening means or components, represented by 138a,b,c,d, extending therefrom that secure the growth module to the nutrient module at the lip, rim or edge 141a comprising the proximal end 141 of the nutrient module. The outer edge of the growth module also comprises a plurality of a second means, generally represented by 139a,b,c,d, for securing or fastening the growth module to the nutrient module, such as snaps, clips or clamp, that are disposed between the primary securing means. The combination of the first and second securing means forms a watertight seal between the modules.

Figure 3:
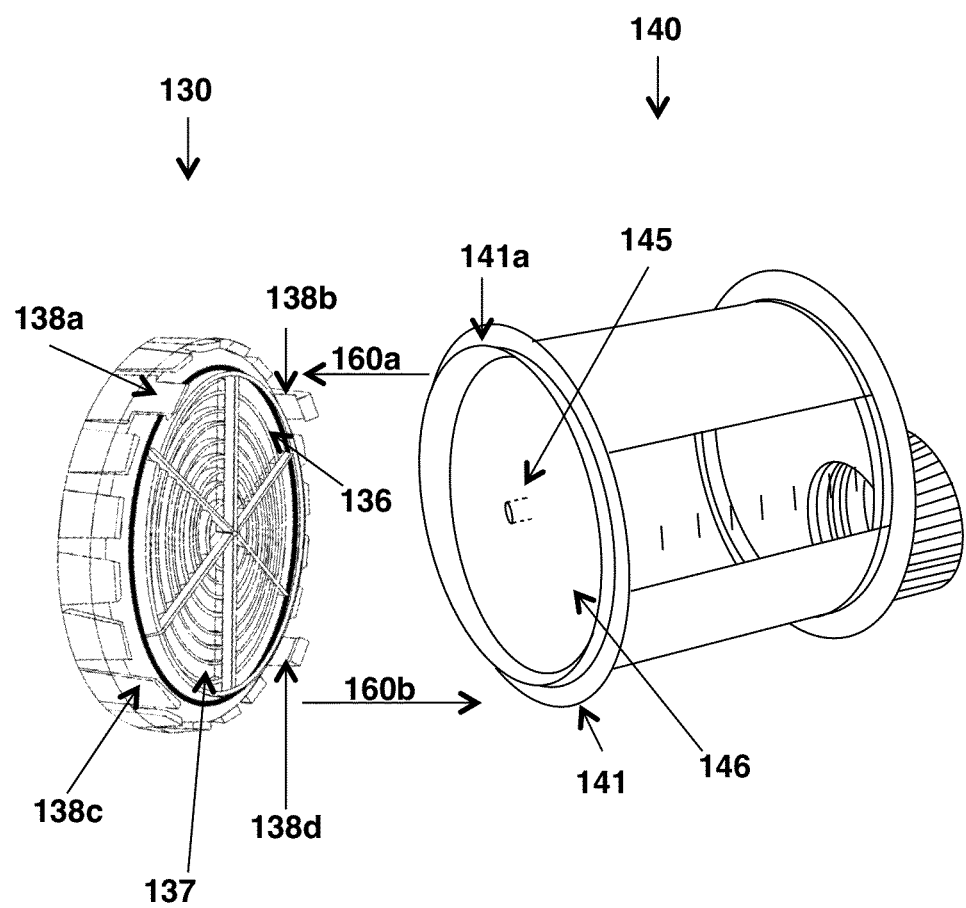
FIG. 3 illustrates the assembly of the growth module with the nutrient module to form the culture unit.
Figure 4:
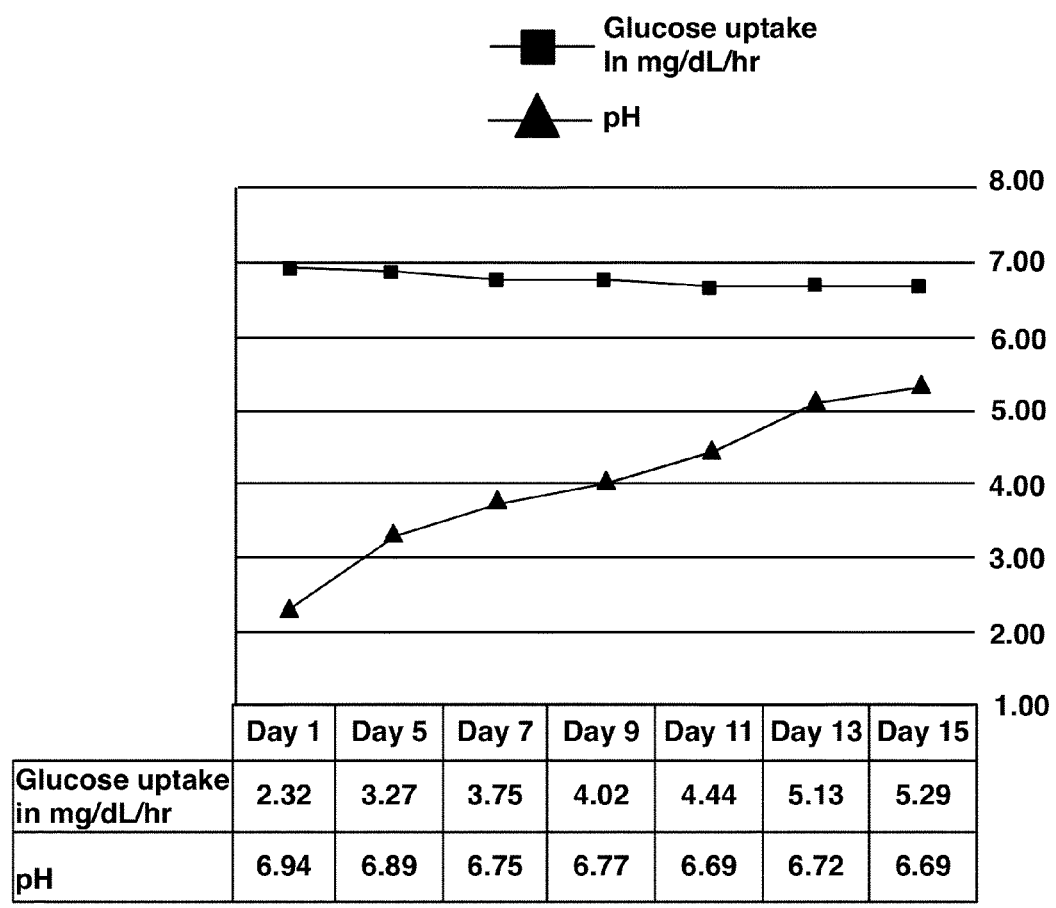
FIG. 4 illustrate culture cell viability parameters of HBTC cells grown with alternating ionic magnetic resonance. Growth module samples were taken prior to weekly changing of the media in the nutrient module and measurements of glucose utilization and culture pH v. time were made.

With continued reference to FIGS. 2A-2B, FIG. 3 illustrates how the growth module 130 is fastened or secured to the nutrient module 140. The gas port or vent 145 and its disposition in relation to the gas-permeable membrane 146 is depicted. One can see that upon fastening the modules together, the baffling system 136 and semi-permeable dialysis membrane 137 in the growth module are in fluid contact with the gas port 145 and gas-permeable membrane 146 in the nutrient module. The fastening means 138a,b,c,d comprise raised beveled edges 139a,b,c,d which can slide or snap over the rim 141a in the nutrient module along 160a,b to secure the growth module therein.

The following example(s) are given for the purpose of illustrating various embodiments of the invention and are not meant to limit the present invention in any fashion.

Example 1

Preparation of Alternating Ionic Magnetic Resonance Culture System
Preparation of Cells for Culture/Medium Under sterile conditions, a seeder culture is started with about 35 to 50 ml of a human or mammalian cell suspension containing approximately $1 \times 10^5$-$5 \times 10^6$ cells/ml in a 50 ml cell culture flask.

The conditions of growing cells in a high density environment requires the use of a high quality media having a minimal concentration of glucose at 4 g/l, and a sufficient buffer component such as $NaHCO_3$ as found in standard media (3.7 g/l) which generally provides buffering capacity for a period of up to 2-10 weeks under standard culture conditions. Because the culture system enables high-density growth, the buffer is generally changed 1 to 2 times per week. The medium in the nutrient module should be replaced as soon as the color starts to change from salmon-pink to a yellowish-pink. Due to the high-density growth inside the growth module, the media will tend to maintain a yellowish color once a critical mass is achieved.

Serum concentration is often critical when eukaryotic cells are grown at high density and should be minimally maintained at levels normally used in stationary culture, approaching 0-80% depending on the cell type. When cells are cultured for the production of secretory molecules, e.g. antibodies, serum concentrations should be 5-30% inside the growth module. Serum concentrations in the nutrient module can often be reduced but should be tested with each individual cell type. Because the use of serum can create foaming problems in the culture system environment, an antifoam agent may be used. Cell types that can be grown without serum should be adapted for such growth prior to growth in the bioreactor.

Adherent cells, such as CHO, HEK 293, BHK, will generally grow first in suspension and then as aggregates. Some adherent cell types will produce secreted products more effectively if grown in the presence of a microcarrier type bead to minimize large aggregates of cells and to optimize cell surface (secretory) area.

Preparation of the Culture System

The culture system is assembled under sterile conditions, preferably in a sterile hood, by attaching to or slipping a pre-sterilized disposable growth module made of polycarbonate inside a reusable nutrient module about ten times larger than the growth module. The growth module is supplied as a pre-sterilized disposable unit pre-packaged in a sterile blister pack and is pre-fitted with a sterile cap. It is inserted into the sterile nutrient module fitted with internal guides to hold the growth module whereby the growth module snaps tightly into place with a liquid tight seal in the specially designed opening. The nutrient module has a separate media opening for periodic exchange of media in the nutrient module which is vented during assembly to vent displaced air. The reusable/disposable nutrient module is comprised of polycarbonate, and sterilized by autoclaving to a maximum of 121° C. for 30 min inside an autoclave bag before assembly or may be gamma sterilized.

Filling the Culture System

The filling steps are done with all of the equipment and solutions equilibrated at the culture temperature to minimize condensation and gas expansion or contraction in the system after assembly. The seeder culture/cell suspension is introduced into the 35 ml growth module with a syringe or pipette through a fill port in the growth module cap taking care to allow for venting of displaced air. This growth module cap has two ports with snap caps comprising rubberized septum caps for syringe inoculations and air removal. One port has a Luer Lock adapter that permits easy filling by a syringe, while the other port is opened to allow air to escape during filling. The growth module is filled completely with the seeder culture and an appropriate media, removing all air from the growth module. The ports are sealed and last traces of air are removed by insertion of an empty syringe with a needle into the rubberized snap caps and withdrawing all air.

The nutrient module is filled to almost full capacity with about 450-500 ml nutrient medium through the inlet port while removing air pressure through the gas-permeable silicone membrane in the nutrient module. A small air space is maintained to provide exchange of gases through the gas port. The inlet port is tightly sealed.

Applying the Electromagnetic Chamber

Once the modules are assembled, filled and sealed, the removable electromagnetic chamber, fitted to the diameter of the nutrient module is slipped over the entire unit from the end distal FIG. 1C to the end with the filling caps and ports. A flexible swivel cord adapter on the chamber enables the entire unit to rotate without interference from the electrical cord that supplies the current to generate the pulsating electromagnetic field. The chamber imparts a time-varying electromagnetic force (square/delta wave, Fourier curve) to the culture system growth chamber and its contents.

Applying the Gravity Vector Randomization Device

The assembled culture system is placed on a gravity vector randomization device inside an incubator chamber set at the temperature adapted for the specific cell culture, which in this case is 35-37° C. and set to rotate the human hybridoma cells at about 5 rpm. The culture system is monitored for leaks and other problems and incubated while continually randomizing the gravity vector until the first sample is taken. Different mammalian cell types require different randomization rates. For example, murine hybridoma cells are generally grown at 5 to 20 rpm, whereas human and transfected cells do well with slightly faster rotation rates of about 10 to 100 rpm. These cell lines are not intended to be limiting to the current invention as the current culture system is intended to be adaptable for the growth of any cell type or tissues that can be adapted to traditional cell culture methods.

Taking Samples and Harvesting

Samples are periodically taken from the culture system in order to assess the growth and development of the cultured material. Before taking samples, the culture system is taken from the incubator, removed from the continually randomized gravity vector device and the electromagnetic chamber is removed. All steps are done quickly to minimize settling of the cells. The culture system is then wiped down to minimize contamination and transferred to a sterile hood. Inside the hood, built up pressure is released by slowly opening the media port in the nutrient module. The growth module can then be sampled by opening the fill port with the Luer lock adapter. The volume removed is replaced with an equal volume of fresh media and the chamber is resealed, reassembled with the electromagnetic chamber and reset on the continually randomized gravity vector device in the incubator chamber.

Changing the Medium in the Nutrient Module

Replacing the spent medium with fresh medium should be done about 1-2 times per week and requires dismantling of the culture system in the same manner as if taking a sample, but the growth module is left unopened. Instead, the nutrient module fill cap is removed and the used medium is emptied by carefully pouring out the contents in a sterile hood. About 350 to 400 ml of fresh media (37° C.) is poured into the nutrient module and reassembled as before. Care is taken to minimize any contamination of the modules or media.

Cell Culture Density

Growth of high-density cells, such as hybridoma cells, requires more oxygen, more nutrients and more frequent removal of waste products and is therefore better accommodated with a continual flow design nutrient module. For example, the oxygen requirement of hybridoma cells at about $10^7$ cells/ml in a 35-50 ml growth module is about 1.75 mg/hr. Some cell lines do not grow to high densities (less than $2 \times 10^7$ cells/ml) but may be cultivated for a longer period of time in the culture system for production and harvest of secreted products with regular changes of medium or a continual flow nutrient module.

Production of Secreted Cell Products

Cell products such as monoclonal antibodies, cytokines, pro-inflammatory molecules, biomolecular markers and all other soluble biochemical products can be produced in a culture system once the cells have been cultured to a critical cell density which depends on the individual properties of the cells cultured. Hybridoma cells typically produce between $4 \times 10^7$ and $7 \times 10^8$ antibody molecules per cell in a 24-hour period.

Genomic Analysis of Tissue-Like Assemblies (TLAs)

RNA from tissue-like assemblies of cells grown in GTSF-2, RPMI 1640, Hams F10, MEM Alpha, L-15, Dulbecco's Modified Eagles Medium (DMEM), Hams F12, Earls MEM, DMEM/F12, or other media appropriate to the cell type with out without alternating ionic magnetic resonance was harvested by removing it from the 3D device and placing in a 50 ml tube. Media was removed and the tissue-like assemblies were washed 3× with sterile PBS. After washing the tissue-like assemblies were frozen at −80 C and stored for transfer to Asuragen Inc. Samples were sent to Asuragen for digestion of the RNA and gene array chip analyses on Affymetrix U133 2.0 plus human genome chips. Digital Chip data was sent to the laboratory and processed by analyses in Genspring software.

3D TLA Growth Kinetics and Glucose Consumption

Metabolic parameters of tissue-like assemblies were measured every 24-48 h over the course of the experiments to monitor a cellular development profile and to monitor the metabolic status of the tissues. Glucose consumption was determined using the iStat clinical blood gas analyzer using an EC8+ cartridge (Abbott Laboratories, Abbott Park, Ill.) according to the manufacturer's instructions (1).

Example 2

Gene Induction in HBTC Cells Grown in the Alternating Ionic Magnetic Resonance Culture System HBTC TLA 3D Cell Culture A culture of cells comprising fibroblasts, mesenchymal and secretory cells (HBTC) were cultured in the alternating ionic magnetic resonance culture system. A mixture of human bronchi and tracheae primary cells (HBTC; fibroblasts and mesenchymal cells) were obtained from the lung mucosa of multiple tissue donors through Cambrex Biosciences (Walkersville, Md.) and were shown to be free of viral contamination by a survey of a panel of standard adventitious viruses (e.g. HIV, hepatitis, herpes) conducted by the supplier (Cambrex). The cells were initially grown as monolayers in human fibronectin coated flasks (BD Biosciences, San Jose, Calif.) and propagated in GTSF-2 media supplemented with 10% fetal bovine serum (FBS). GTSF-2 media, initially described in U.S. Pat. No. 5,846,807, is a tri-sugar-based growth medium containing glucose, galactose and fructose. U.S. Pat. No. 5,846,807 is herein incorporated by reference in its entirety.

The monolayers were grown in a Form a humidified $CO_2$ incubator with 95% air and 5% $CO_2$ at constant atmosphere and at 37° C. The HBTC cells were passaged using enzymatic dissociation with a solution of 0.1% trypsin and 0.1% EDTA for 15 minutes at 37° C. After incubation with the appropriate enzymes, the cells were transferred to 50 ml Corning conical centrifuge tubes and centrifuged at 800 g for 10 minutes. The pelleted cells were suspended in fresh GTSF-2 medium and diluted into T-75 flasks using 30 ml of fresh growth medium.

The culture assembly was inoculated with HBTC (mesenchymal) cells and grown for several weeks. HBTC cells were first removed from the T flasks by enzymatic digestion, washed once with calcium- and magnesium-free phosphate-buffered saline (CMF-PBS), and assayed for viability by trypan blue dye exclusion (Gibco). Cells were held on ice in fresh growth medium prior to inoculation of the culture assembly. The primary inoculum for the culture experiment included $2 \times 10^5$ cells/ml HBTC cells, which were added to fresh GTSF-2 media in a 35-ml growth module with 5 mg/ml of Cytodex-3 (Type I, collagen-coated cyclodextran) microcarriers having a diameter of 120 mm (Pharmacia, Piscataway, N.J., USA). The 450 ml nutrient module was filled with fresh GTSF-2 media, the culture assembly was sealed as described above.

Briefly, the alternating ionic magnetic resonance is supplied to the culture unit by encompassing the culture assembly with the removable and adjustable alternating ionic magnetic resonance coil. At increasing frequencies cultured cells and media are exposed to an alternating ionic magnetic resonance signal at fundamental intervals of 10, 14, 15, 16 and 32 Hz including the harmonic intervals of each of these extending to 256 Hz and incorporating all harmonics of the aforementioned fundamental frequencies to infinity in the form of a square wave of 0.01-5000 mA. The alternating ionic magnetic resonance chamber providing the electromagnetic protocol was placed around the culture device and a series of stepped resonance pulses at approximately 500 msec intervals was applied to the outside of the culture assembly. The culture assembly and the unit was connected to a continuously randomized gravity device and grown in a Form a humidified $CO_2$ incubator with 94.5% air and 5.5% $CO_2$ providing constant atmosphere at 35.0° C. to mimic that of the nasopharyngeal epithelium. The HBTC cultures were allowed to grow for a minimum of 24 hours before the medium was changed. Thereafter, fresh medium was replenished by replacing 65-100% of the spent medium within the nutrient module once every 96-168 hour period.

At this point, the media for the culture experiments comprised GTSF-2 supplemented with 10% fetal bovine serum. As the cells proliferated, metabolic requirements increased, and the fresh medium was routinely supplemented with an additional 100 mg/dl of glucose.

Figure 5:
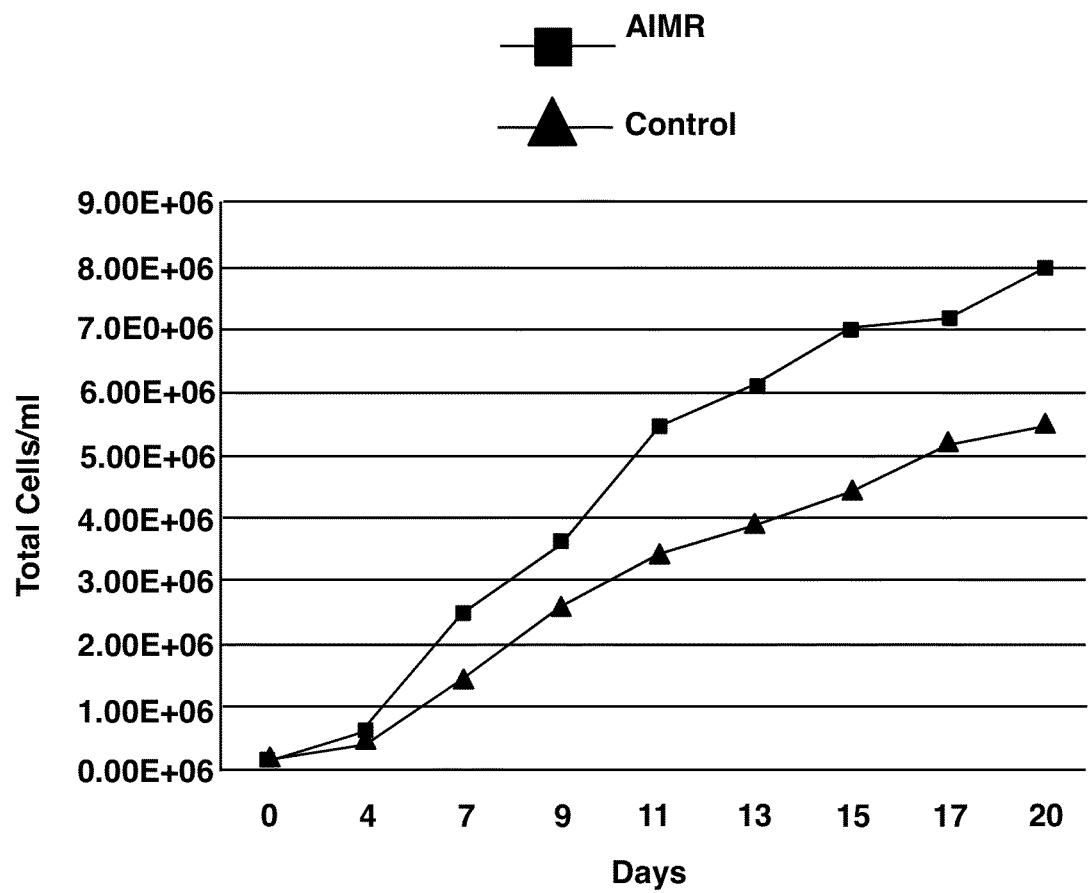
FIG. 5 is a cell growth and tissue assembly curve for HBTC cells with and without exposure to alternating ionic magnetic resonance over a twenty day growth period.

The culture was sampled periodically over the course of the experiment, generally at 24-48 hour time points, in order to establish a cellular development profile. The parameters of glucose utilization (FIG. 5A) and pH (FIG. 5B) were surveyed via iStat™ clinical blood gas analyzer to determine the relative progress and health of the cultures and the rate of cellular growth and viability.

Figure 6A:
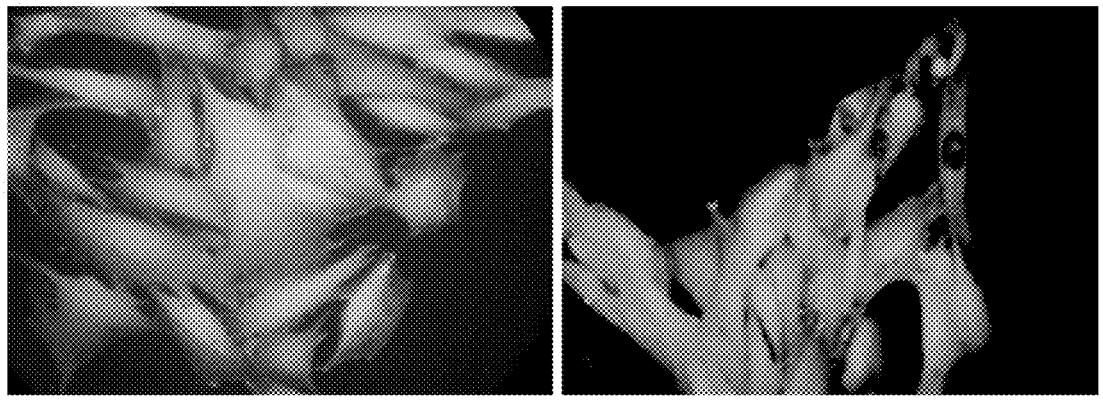
FIGS. 6A-6D are calcium and potassium ion transport micrographs of HBTC cells grown in alternating ionic magnetic resonance culture apparatus.
Figure 6B:
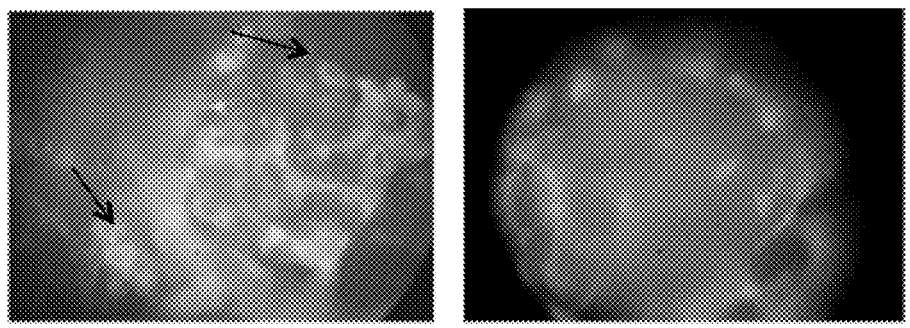
Figure 6B:
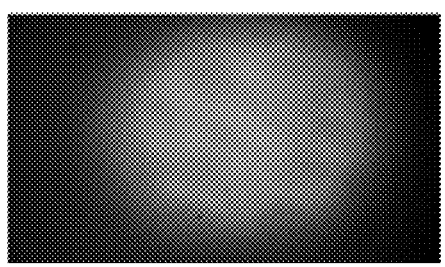
Figure 6C:
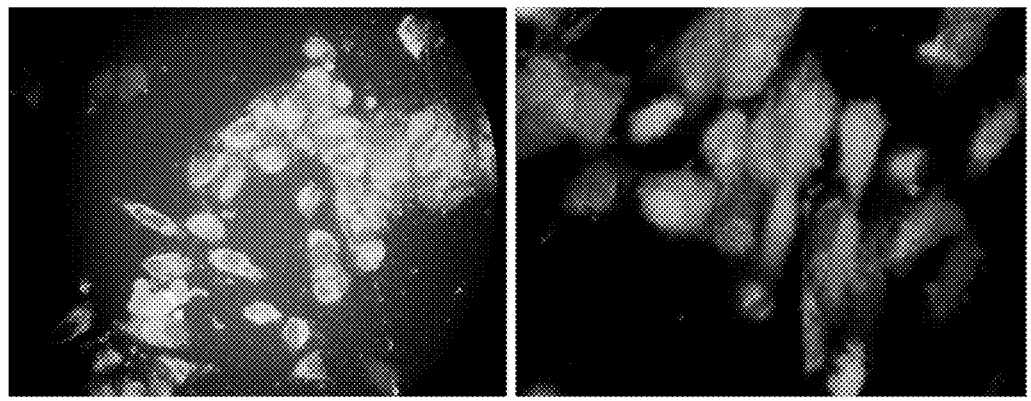
Figure 6D:
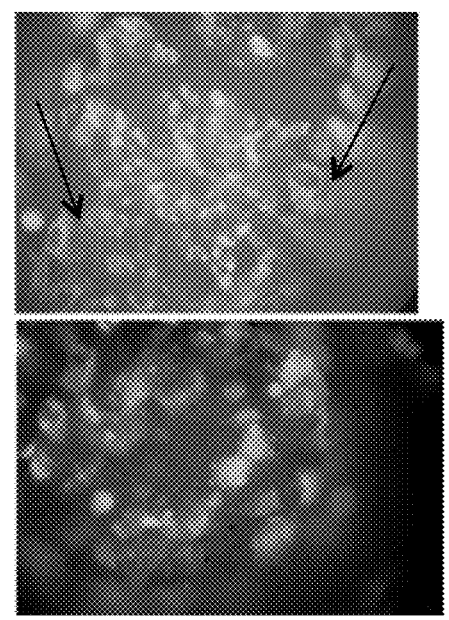
Figure 6D:
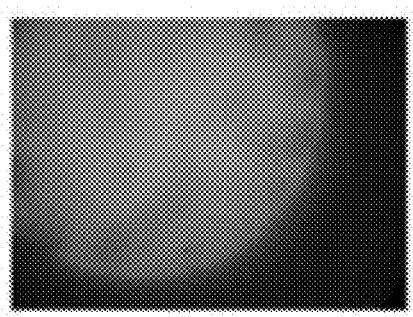

The cells were monitored as shown in FIGS. 6A to 6D. FIG. 6A shows photos of the HBTC cells grown in T-flasks (passaged as necessary to maintain growth over a 20-day period) that have been infused with the calcium binding fluorescent dye, Fura-2AM. The cells on the left were exposed to multi-variant electromagnetic frequency field for the entirety of the 20-day growth period. Cells in the right panel were not exposed to an electromagnetic field. Exposure to alternating ionic magnetic resonance altered the cellular distribution of calcium ions. FIG. 6B shows HBTC cells grown on cultisphere or Cytodex-3 microcarriers in the alternating ionic magnetic resonance bioreactor for 21 days. The upper left panel shows cells exposed to alternating ionic magnetic resonance for the entire growth period; the cells on the right were not exposed to an electromagnetic field. Tissue-like assemblies of cells and microcarrier beads (tissue-like assemblies) were treated with Fura-2AM. Although the microcarriers shown retain background levels of fluorescence as evidenced by the photo in the bottom control panel showing the microcarrier alone, the cells exposed to alternating ionic magnetic resonance emit a significant signal above background levels. Arrows indicate clusters of cells attached to, but not atop a microcarrier bead. FIG. 6C is similar to cells shown in FIG. 6A, with HBTC cells grown with (left) or without (right) alternating ionic magnetic resonance, but infused with the potassium binding fluorescent dye, PBFI-2 AM. FIG. 6D illustrates potassium ion staining of cells grown in the presence of microcarrier beads either with (top) or without (middle) alternating ionic magnetic resonance compared to a microcarrier alone control treated with PBFI-AM (bottom).

Gene Induction in the Alternating Ionic Magnetic Resonance-Grown HBTC TLAs

HBTC cells grown in the alternating ionic magnetic resonance culture system demonstrate up-regulation of genes within specific gene families, including levels of expression for various transport and regenerative genes. Table 1 lists genes up-regulated in an alternating ionic magnetic resonance field and provides the fold increase relative to level of gene expression in cells grown without a magnetic resonance field.

TABLE 1

Alternating Ionic Magnetic Resonance Initiated Gene Up-Regulation

| GENE SYMBOL | GENE FAMILY TRANSPORT FAMILY GENES GENE NAME | FOLD INCREASE |
|---|---|---|
| (1) Calcium Ion Transport | | |
| KCNMB1 | Potassium large conductance Calcium-activated channel, subfamily M, beta member 1 | +62 |
| CABP1 | calcium binding protein 1 (calbrain) | +52 |
| CACNG1 | calcium channel, voltage-dependent, gamma subunit 1 | +46 |
| CABP2 | calcium binding protein 2 | +36 |
| SLC24A3 | solute carrier family 24 (sodium/potassium/calcium exchanger), member 3 | +12 |
| CACNA1C | calcium channel, voltage-dependent, L type, alpha 1C subunit | +3.6 |
| TACSTD | tumor-associated calcium signal transducer 2 | +2.8 |
| CACNB1 | calcium channel, voltage-dependent, beta 1 subunit | +7.3 |
| CALB3 | calbindin 3, vitamin D-dependent calcium binding protein | +4.2 |
| KCNMA1 | potassium large conductance calcium-activated channel, subfamily M, alpha member 1 | +3.0 |
| CACL2 | chloride channel, calcium activated, family member 2 | +2.5 |
| CAMK2A | calcium/calmodulin-dependent protein kinase (CaM kinase) II alpha | +2.5 |
| S100A5 | S100 calcium binding protein A5 | +2.3 |
| (2) Potassium Ion Transport | | |
| KCNMB1 | Potassium large conductance Calcium-activated channel, subfamily M, beta member 1 | +61 |
| KCND3 | potassium voltage-gated channel, Shal-related subfamily, member 3 | +21 |
| SLC24A3 | solute carrier family 24 (sodium/potassium/calcium exchanger), member 3 | +8.6 |
| KCNK15 | potassium channel, subfamily K, member 15 | +3.7 |
| KCNK3 | potassium channel, subfamily K, member 3 | +2.1 |
| KCNJ12 | potassium inwardly-rectifying channel, subfamily J, member 12 | +7.6 |
| KCNQ1 | potassium voltage-gated channel, KQT-like subfamily, member 1 | +3.3 |
| KCNAB1 | potassium voltage-gated channel, shaker-related subfamily, beta member 1 | +3.1 |
| KCND3 | potassium voltage-gated channel, Shal-related subfamily, member 3 | +3.0 |
| KCND2 | potassium voltage-gated channel, Shal-related subfamily, member 2 | +2.8 |
| SLC12A5 | solute carrier family 12, potassium-chloride transporter member 5 | +2.7 |
| KCNJ5 | potassium inwardly-rectifying channel, subfamily J, member 5 | +2.5 |
| SLC24A1 | solute carrier family 24 (sodium/potassium/calcium exchanger, member 1 | +2.2 |
| KCNE1L | potassium voltage-gated channel, Isk-related family, member 1-like | +2.2 |
| KCNK7 | potassium channel, subfamily K, member 7 | +2.0 |
| KCNK4 | potassium channel, subfamily K, member 4 | +1.9 |
| (3) ATPase Transport | | |
| ATP6V0A4 | ATPase, H+ transporting, lysosomal V0 subunit a isoform 4 | +32 |
| ATP2A3 | ATPase, Ca++ transporting, ubiquitous | +14 |
| ATP1A2 | ATPase, Na+/K+ transporting, alpha 2 (+) polypeptide | +6.5 |
| SERCA3 | ATPase, Ca++ transporting, ubiquitous | +6 |
| ATP2A1 | ATPase, Ca++ transporting, cardiac muscle, fast twitch 1) | +13 |

TABLE 1-continued

Alternating Ionic Magnetic Resonance Initiated Gene Up-Regulation

| | | |
|---|---|---|
| ATP6V0A2 | ATPase, H+ transporting, lysosomal V0 subunit a isoform 2 | +7.7 |
| ATPase | mRNA sequence | +7.2 |
| ATP11A | ATPase, Class VI, type 11A | +5.6 |
| ATP-binding | Cassette, sub-family A (ABC1), member 6 | +4.7 |
| TAP2 | transporter 2, ATP-binding cassette, sub-family B (MDR/TAP) | +4.5 |
| ABCC9 | ATP-binding cassette, sub-family C (CFTR/MRP), member 9 | +2.7 |
| ATP4B | ATPase, H+/K+ exchanging, beta polypeptide | +2.5 |
| ATP8A1 | ATPase, aminophospholipid transporter (APLT), Class I, type 8A, member 1 | +2.5 |
| ABCA8 | ATP-binding cassette, sub-family A (ABC1), member 8 | +2.4 |
| ATP6V1B1 | ATPase, H+ transporting, lysosomal 56/58 kDa, V1 subunit B, isoform 1 | +2.4 |
| ATP5G2 ATP synthase | , H+ transporting, mitochondrial F0 complex, subunit c (subunit 9), isoform 2 | +2.0 |
| ATP1B4 | ATPase, (Na+)/K+ transporting, beta 4 polypeptide | +1.9 |

REGENERATION GENES

| GENE SYMBOL | GENE NAME | |
|---|---|---|
| (1) WNTs Family | | |
| WNT2 | wingless-type MMTV integration site family member 2 | +21038 |
| WNT16 | wingless-type MMTV integration site family member 16 | +180.8 |
| WNT3 | inducible signaling pathway protein 3 | +45.8 |
| WNT4 | | +78.8 |
| WNT8B | | +3.3 |
| WNT1 | | +1.7 |
| (2) Bone Morphogenetic Protein Family | | |
| (BMP2) | Bone Morphogenetic Protein 2 | +166.6 |
| (BMP5) | Bone Morphogenetic Protein 5 | +88.0 |
| BMP-2 inducible kinase | BMP inducible kinase | +5.5 |
| BMPY | Bone Morphogenetic Protein Y | +2.4 |
| (BMP6) | Bone Morphogenetic Protein 6 | +1.6 |
| (3) Catenin Family | | |
| Catenin | cadherin-associated protein, delta 2 (neural plakophilin-related arm-repeat protein) | +38.3 |
| Catenin | | +2.1 |
| (4) Forkhead Box Family | | |
| FOXI1 | Forkhead Box I1 | +60.4 |
| FOXA2 | Forkhead Box A2 | +9.0 |
| FOXD1 | Forkhead Box D1 | +3.4 |
| FOXA1 | Forkhead Box A1 | +2.0 |
| FOXM1 | Forkhead Box M1 | +1.6 |
| (5) SOX (SRY (Sex Determining Region Y)-BOX2) Family | | |
| SOX2 | | +2.2 |
| SOX3 | | +1.9 |
| SOX29 | | +1.8 |
| SOX17 | | +1.7 |
| (6) Transforming Growth Factor (TGF) Family | | |
| TGFBR2 | transforming growth factor, beta receptor II | +1.9 |
| TGFA | transforming growth factor, alpha) | +1.9 |
| TGIF2 | TGFB-induced factor 2 (TALE family homeobox) | +1.7 |

TABLE 1-continued

Alternating Ionic Magnetic Resonance Initiated Gene Up-Regulation

| (7) Parathyroid Hormone (PTH) Family | | |
|---|---|---|
| PTH | parathyroid hormone | +180 |
| PTHLH | parathyroid hormone-like hormone | +1.8 |
| PTHR2 | parathyroid hormone receptor 2 | +1.6 |

Example 3

Gene Induction in NHNP and HBE Cells Grown in the Alternating Ionic Magnetic Resonance Culture System
NHNP TLA 3D Cell Culture NHNP cells were obtained from Lonza (Walkersville, Md., USA) and propagated in GTSF-2, a unique media containing glucose, galactose and fructose supplemented with 10% fetal bovine serum (FBS), at 37° C. under a 5% $CO_2$ atmosphere (2-4). NHNP cells were initially grown as monolayers in human fibronectin-coated flasks (BD Biosciences, San Jose, Calif.) and pooled from at least five donors, as described previously (5). NHNP cell cultures were expanded, tested for viral contaminants as pre-certified by the manufacturer's production criteria (Lonza), and cryo-preserved in liquid nitrogen. Three-dimensional (3D) NHNP TLAs were generated by seeding $3 \times 10^5$ NHNP cells/ml onto 3 mg/ml Cultispher beads (Sigma-Aldrich, St. Louis, Mo.) into a 55 ml rotating wall vessel bioreactor (RWV; Synthecon, Houston, Tex.) or into the culture unit of the alternating ionic magnetic resonance culture apparatus and grown at 37° C. under a 5% $CO_2$. Cells were allowed to attach to the beads for 48 h in the bioreactor before re-feeding with GTSF-2 containing 10% FBS. To maintain the TLA cultures within normal human physiological blood chemistry parameters (pH 7.2 and a glucose concentration of 80-120 mg/dL), 20-90% of the media was replaced as required with fresh GTSF2 media every 48 h, facilitating efficient tissue-like assembly tissue growth and maturation prior to VZV infection. All metabolic determinations were made using an iStat hand held blood gas analyzer (Abbott Laboratories, Abbott Park, Ill.). Flow cytometry analysis confirmed that after 180 days in culture, NHNP TLAs expressed neuronal progenitor markers CXCR4, CD133, CD105-Endoglin, CD 90-Thy-1 and CD49f-α6 Integrin at levels comparable to a parental NHNP (2D) cell population.

HBE TLA 3D Cell Culture

Mesenchymal cells (HBTC) from human bronchi and tracheae were obtained from three donors through Cambrex Biosciences (Walkersville, Md.). LLC-MK2 and BEAS-2B epithelial cells (6) were obtained from ATCC (Manassas, Va.). BEAS-2B cells were used instead of primary cells to provide consistency from batch to batch. BEAS-2B and HBTC cells were maintained in GTSF-2 medium with 7% fetal bovine serum (7) in human fibronectin coated flasks (BD Biosciences, San Jose, Calif.). Vero, HEp-2, and LLC-MK2 cells were grown at 37° C. in Eagle's modified minimum essential medium supplemented with 2 mM non-essential amino acids, 100 units penicillin, 100 μg/ml streptomycin, 0.25 μg/ml amphotericin B, 10% fetal bovine serum, 2 mM L-glutamine, and 25 mM HEPES buffer (Gibco-BRL, Gaithersburg, Md.).

To construct 3D HBE tissue-like assembly cultures, HBTC cells from a monolayer culture were seeded at $2 \times 105$ cells/mL into a 55-mL rotating wall vessel (RWV) (Synthecon, Houston, Tex.) or into the culture unit of the alternating ionic magnetic resonance culture apparatus with 4-5 mg/mL of Cytodex-3 microcarriers, type I collagen-coated cyclodextran microcarriers (Pharmacia, Piscataway, N.J.) at 35° C. Cultures were allowed to grow for a minimum of 48 hours before the medium was changed. BEAS-2B cells were seeded at 2×10$^5$ cells/mL 4 to 6 days after HBTCCytodex 3 microcarrier aggregates were formed. Thereafter, approximately 65% of the media was replaced every 20 to 24 hours. As metabolic requirements increased, the glucose concentration in GTSF-2 medium was increased to 200 mg/dL. Tissue-like assembly cultures were grown in RWV to 1 to 2 mm in diameter using the rotary cell culture system (Synthecon, Houston, Tex.) or into the culture unit of the alternating ionic magnetic resonance culture apparatus at 35° C. with appropriate rotation rate for aggregate suspension. Cell numbers were determined after treating the tissue-like assemblies with 2000 U/mL type I collagenase (Invitrogen, Carlsbad, Calif.) at 37° C. for 10 minutes. Expression levels of epithelial markers in TLAs are very similar to the levels in normal human lung than in 2D BEAS-2B and HBTC cells.

Alternating Ionic Magnetic Resonance-Exposed HBE and NHNP TLAs

A set of human bronchial epithelial (HBE) tissue-like assembly samples and a set of normal human neural progenitor (NHNP) tissue-like assembly samples, each set contained in at least 3 rotating wall vessels (RWVs) were exposed to an alternating ionic magnetic resonance stimulation field of predetermined profile. The profile substantially comprises a biphasic, square wave with a frequency of about ~10 Hz, a wavelength of about 500 ms, a rising slew rate between about 0.1 T/s (1.0 kG/s) to about 0.50 T/s (5.0 kG/s), a falling slew rate between about 0.50 T/s (5.0 kG/s) and about 2.0 T/s (20.0 kG/s), a dwell time of about 10% after each burst, a duty cycle of about 80% on and about 20% off, and a resultant B-Field magnitude of about 100 μT (1.0 G). The experiment was conducted at ~10 Hz. For reference purposes, the frequency of Earth's geomagnetic field is 7.83 Hz, thus the experiment satisfies the criteria of being appreciably different from the background magnetic field. Exposure was continuous for the duration of a period of about 15-90 days or about 360-2160 hours. A gene fold change analysis, as describe in Example 1, was conducted for the HBE and NHNP TLA samples exposed to the alternating ionic magnetic resonance stimulation field.

Gene Induction in Alternating Ionic Magnetic Resonance-Grown HBE and NHNP TLAs

Although the HBE and NHNP tissue-like assemblies responded differently when exposed to an alternating ionic magnetic resonance field under substantially identical conditions, unexpectedly, in both sets virally-associated and viral oncogenes were activated and their expression levels were upregulated. Most of the differentially regulated genes are related to the ability of viruses to be absorbed or introduced into the human cell to enable replication and proliferation. Table 2 lists the up-regulated viral genes initiated by alternating ionic magnetic resonance.

TABLE 2

Alternating Ionic Magnetic Resonance Initiated Viral Gene Up-Regulation

| GENE SYMBOL | GENE NAME | FOLD INCREASE |
|---|---|---|
| HBE TLA GENES | | |
| RAB6A | RAB6A virus associated | 2.7991202 |
| RAB5B | RAB5B virus associated | 1.5721819 |
| IVNS1ABP | influenza virus NS1A binding protein | 1.5685624 |
| JUN | jun oncogene | 1.6782385 |
| JUNB | jun B proto-oncogene | 1.5822183 |
| HTATSF1 | HIV-1 Tat specific factor 1 | 1.8373269 |
| FOSB | FBJ murine osteosarcoma viral oncogene homolog B | 1.5298892 |
| JUND | jun D proto-oncogene | 3.2985632 |
| CXADR | coxsackie virus and adenovirus receptor | 1.8511372 |
| EVI2A | ecotropic viral integration site 2A | 1.922923 |
| EBI2 | Epstein-Barr virus induced gene 2 (lymphocyte-specific G protein-coupled receptor) | 1.7887306 |
| IVNS1ABP | influenza virus NS1A binding protein | 1.7672802 |
| AKT1 | v-akt murine thymoma viral oncogene homolog 1 | 1.5862192 |
| FOS | v-fos FBJ murine osteosarcoma viral oncogene homolog | 4.55682 |
| UBE3A | ubiquitin protein ligase E3A (human papilloma virus E6-associated protein | 1.5529021 |
| EVI2B | ecotropic viral integration site 2B | 1.566628 |
| RRAS | related RAS viral (r-ras) oncogene homolog | 1.6267682 |
| HRB | HIV-1 Rev binding protein | 1.6248319 |
| JUND | jun D proto-oncogene | 2.2347317 |
| FYN | FYN oncogene related to SRC | 1.8570358 |
| ITPR1 | inositol 1 | 1.5927685 |
| RAB23 | RAB23 | 1.7071296 |
| AKT3 | v-akt murine thymoma viral oncogene homolog 3 (protein kinase B | 1.8035016 |
| BIRC6 | baculoviral IAP repeat-containing 6 (apollon) | 1.5996437 |
| THRB | thyroid hormone receptor | 1.7461618 |
| TPR | translocated promoter region (to activated MET oncogene) | 1.7921942 |
| NHNP TLA GENES | | |
| ETS2 | v-ets erythroblastosis virus E26 oncogene homolog 2 (avian) | 1.5718486 |
| JUNB | jun B proto-oncogene | 2.720869 |
| EGFR | epidermal growth factor receptor (erythroblastic leukemia viral (v-erb-b) oncogene homolog | 2.6352847 |

TABLE 2-continued

Alternating Ionic Magnetic Resonance Initiated Viral Gene Up-Regulation

| GENE SYMBOL | GENE NAME | FOLD INCREASE |
|---|---|---|
| BIRC5 | baculoviral IAP repeat-containing 5 (survivin) | 1.6022671 |
| FOSB | FBJ murine osteosarcoma viral oncogene homolog B | 2.0152645 |
| PVRL2 | poliovirus receptor-related 2 (herpesvirus entry mediator B) | 1.6020694 |
| SKIV2L | superkiller viralicidic activity 2-like (S. cerevisiae) | 1.520639 |
| FOS | v-fos FBJ murine osteosarcoma viral oncogene homolog | 5.8558683 |
| TNFRSF14 | tumor necrosis factor receptor superfamily member 14 (herpesvirus entry mediator) | 1.8052368 |
| PVR | poliovirus receptor | 2.9330401 |
| THRA | thyroid hormone receptor (Alpha (erythroblastic leukemia viral (v-erb-a) oncogene homolog | 1.5989169 |
| MOV10 | Mov10 Maloney Leukemia Virus 10 | 1.8294989 |
| PVRL2 | poliovirus receptor-related 2 (herpesvirus entry mediator B) | 1.5439448 |
| ISY1 /// RAB43 | ISY1 splicing factor homolog (S. cerevisiae) /// RAB43 | 1.802375 |
| MRVI1 | murine retrovirus integration site 1 homolog | 2.84193 |
| MAFK | v-maf musculoaponeurotic fibrosarcoma oncogene homolog K (avian) | 1.6252148 |
| RAB4B | RAS oncogene family | 1.5139388 |
| MRVI1 | murine retrovirus integration site 1 homolog | 2.0572836 |
| RAB7B | RAS oncogene family | 1.5806108 |
| LOC401233 | similar to HIV TAT specific factor 1; cofactor required for Tat activation of HIV-1 transcription | 2.2209923 |

Example 4

3-Dimensional TLA Models of Viral Infection
v63G/70R Infection of NHNP TLAs

Varicella zoster virus (VZV) was propagated in human melanoma cells (MeWo, American Type Culture Collection, ATCC, Manassas, Va.) in Dulbecco's minimal essential medium supplemented with 10% fetal bovine serum, 100 U/ml penicillin and 0.1 mg/ml streptomycin (Sigma-Aldrich, St. Louis, Mo.) at 37° C. under a 5% $CO_2$ (8). Wild-type and recombinant viruses were passaged on MeWo cells by co-cultivation of infected with uninfected cells at a ratio of 1/5 (9). MeWo cells for the infection of NHNP cultures were adapted to GTSF2 medium over two passages prior to harvest of VZV.

Cell free VZV was used for the NHNP TLA infections to avoid transfer of any infected MeWo cells to the TLA culture (10). Briefly, infected cells were harvested at 96 h post-infection (p.i.) and resuspended in reticulocyte standard buffer (10 mM NaCl, 1.5 mM $MgCl_2$, 10 mM Tris-HCl, pH 7.4). Cells were disrupted by Dounce (type A) homogenization (Cole-Parmer, Vernon Hills, Ill.) and clarified by centrifugation at 900×g for 15 min.

NHNP tissue-like assemblies were infected in the RWV with cell-free VZV at a multiplicity of infection (MOI) of 0.1 by absorption at room temp for 30 min in 20 ml GTSF-2. Then, the RWVs were filled with fresh GTSF-2/10% FBS and transferred to a humidified incubator with under 5% $CO_2$ atmosphere at 37° C. Every 24 h p.i., 55-65% of the culture media was replaced with fresh GTSF-2 containing 10% FBS. Samples were collected approximately every other day for ~70 days to determine viral genome copies utilizing a dually tagged v63G/70R recombinant.

Dually tagged v63G/70R was able to efficiently infect NHNP tissue-like assemblies, as evidenced by an approximate 50-fold increase in VZV genome copies from 0 to 18 days post-infection (dpi). After 18 dpi, VZV genome copy numbers remained constant, indicating that the virus had established equilibrium between de novo virus DNA replication and degradation. Glucose utilization was used to monitor the metabolic activity of infected and uninfected 3D NHNP tissue-like assemblies and MeWo cultures. Each culture was initially maintained for 39 days to establish a baseline glucose consumption rate before and after infection with v63G/70R. Upon infection, glucose utilization rapidly declined in MeWo cells, as cell death, likely as a consequence of lytic VZV replication, was evident microscopically (data not shown). In contrast, glucose uptake in NHNP tissue-like assemblies was not altered as a response to VZV infection, suggesting that limited, if any, lytic VZV infection occurred. Confocal analysis of v63G infected NHNP tissue-like assemblies at 27 dpi revealed that the progenitor neuronal marker Nestin and the mature neuronal marker β Tubulin-Ill colocalized with GFP, indicating that VZV preferentially established a persistent infection in these cells.

GFP/RFP ratios in v63G/70R infected NHNP tissue-like assemblies remained unaltered for at least 69 days in culture, suggesting that the VZV genome is stably maintained in NHNP tissue-like assemblies. In addition, confocal microscopy confirmed that both ORF63-eGFP and ORF70-mRFP are expressed in NHNP tissue-like assembly cultures infected with v63G/70R. A stable viral genome is preserved for an extended period in NHNP tissue-like assemblies.

Paramyxovirus Infection of HBE TLAs

Tissue-like assemblies were inoculated at a MOI of 0.1 with both wtPIV3 and attenuated PIV3 viruses to achieve an effective MOI of 1 for the cells on the outer surface. After virus absorption at room temperature for 1 hour, HBE TLA cultures were washed three times with DPBS (Invitrogen, Carlsbad, Calif.) and fed with media. All air bubbles were removed from the RWV before rotation to eliminate shearing of the cells (7). Approximately 65% of the culture media was replaced every 48 hours. For virus titration, samples were collected on days 0, 2, 4, 6, 8, and 10. In HBE tissue-like assemblies, replication of wtPIV3 approached 7.5 log 10 pfu/mL by day 6 pi, while the attenuated virus replicated maximally to 5.5 log 10 pfu/ml on day six. Reduced replication in attenuated viruses may be due to a slower progression from layer to layer in the 3D HBE tissue-like assemblies. Increased secretion of at least 2-fold of cytokines, chemokines and colony stimulating factors was found for interleukin-1, -4, -6, and -8, for RANTES, MIP-1a, MIP-1, and G-CSF.

The following references are cited herein.
1. Vertrees et al. Cancer Biol Ther 8:356-365 (2009).
2. Lelkes et al. In Vitro Cell Dev Biol Anim 33:344-351 (1997).
3. Goodwin, T. J. U.S. Pat. No. 5,846,807 (1998).
4. Goodwin, T. J. U.S. Pat. No. 5,858,783 (1997).
5. Goodwin, T. J. Physiological and Molecular Genetic Effects of Time-Varying Electromagnetic Fields on Human Neuronal Cells. NASA Tech Paper, TP-2003-212054 (2003).
6. Ke et al. *Differentiation* 38:60-66 (1988).
7. Goodwin et al. *Proc Soc Exp Biol Med* 202:181-192 (1993).
8. Grose et al. J Gen Virol 43:15-27 (1979).
9. Cohrs et al. J Virol 76:7228-7238 (2002).
10. Grose et al. Infect Immun 19:199-203 (1978).

While the present invention is described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention set forth in the following claims.

What is claimed is:

1. A culture system for culturing cells, tissue or organoid bodies, comprising:
    a nutrient module having a proximal end;
        a first gas-permeable membrane disposed on the proximal end;
        a gas port fitted onto the first-gas permeable membrane; and
        a first sealable opening on the distal end
    a growth module having a proximal end comprising a second gas-permeable membrane with a plurality of inlet/outlet ports disposed thereon and a distal end comprising a baffling system and a semi-permeable membrane, said growth module fluidly connected with the first gas-permeable membrane in the nutrient module;
    a randomizing adapter having an open proximal end of a diameter sufficient to receive the nutrient module therein, said distal end of the nutrient module adaptable to electrically connect with a randomizing mechanism comprising the adapter such that the gravity vector of the growth module fluidly connected to the nutrient module is continually randomized;
    a removable open-ended substantially cylindrical electromagnetic chamber with a diameter sufficient to receive at least the growth module therein and comprising an electrically conductive wire wound on a square, oval or cylindrical-shaped scaffold thereon; and
    an electrical conversion device comprising a waveform generator, an amplifier and an antenna configured to generate and convert a pulsating time-varying electromagnetic current into a pulsating overapping or fluctuating alternating ionic magnetic resonance frequency field at one or more modal intervals spanning about 6.5 Hz and ranging from about 7.8 Hz to 59.9 Hz with a filed strength of about 0.01 Gauss to about 10,000 Gauss connected electrically to the electromagnetic chamber.

2. The culture system of claim 1, wherein one or both of the nutrient module and the growth module are disposable.

3. The culture system of claim 1, wherein said nutrient module, said growth module and said randomizing adapter are sterilizable.

4. The culture system of claim 1, wherein the cells are virally-infected cells, bacterially-infected cells, normal tissue cells, or an organoid body.

5. The culture system of claim 1, wherein the overlapping or fluctuating alternating ionic magnetic resonance frequencies produced are about 10, 14, 15, 16, or 32 Hz.

6. The culture system of claim 1, wherein one or more of the alternating ionic magnetic resonance frequencies produced fluctuate between about 8 and 14 Hz.

7. The culture system of claim 1, wherein the electrically conductive wire is copper wire or ferromagnetic wire wrapped about a non-conductive or conductive core at about 5 to about 500 turns per inch.

8. The culture system of claim 1, wherein the alternating ionic magnetic resonance field has a field strength of about 0.01 Gauss to about 5,000 Gauss.

* * * * *